(12) United States Patent
Ko et al.

(10) Patent No.: US 7,550,486 B2
(45) Date of Patent: *Jun. 23, 2009

(54) N-UREIDOALKYL-PIPERIDINES AS MODULATORS OF CHEMOKINE RECEPTOR ACTIVITY

(75) Inventors: Soo S. Ko, Hockessin, DE (US); George V. Delucca, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/972,649

(22) Filed: Jan. 11, 2008

(65) Prior Publication Data

US 2008/0132523 A1 Jun. 5, 2008

Related U.S. Application Data

(63) Continuation of application No. 10/865,417, filed on Jun. 10, 2004, now Pat. No. 7,351,720.

(60) Provisional application No. 60/478,022, filed on Jun. 12, 2003.

(51) Int. Cl.
*A61K 31/445* (2006.01)
*C07D 211/14* (2006.01)

(52) U.S. Cl. .............. 514/331; 546/231; 546/194; 546/199; 546/201; 546/209; 544/129; 514/235.5; 514/326

(58) Field of Classification Search .......... 514/331, 514/326, 235.5; 546/231, 194, 199, 201, 546/203, 209; 544/129
See application file for complete search history.

(56) References Cited

U.S. PATENT DOCUMENTS 6,331,541 B1 12/2001 Ko et al.
6,444,686 B1 9/2002 Ko et al.
6,486,180 B1 11/2002 Ko et al.
6,492,400 B1 12/2002 Ko et al.
6,525,069 B1 2/2003 Ko et al.
6,605,623 B1 8/2003 Ko et al.
6,638,950 B2 10/2003 Duncia et al.
7,351,720 B2 * 4/2008 Ko et al. .............. 514/326

FOREIGN PATENT DOCUMENTS

WO WO00/35451 6/2000
WO WO01/98268 12/2001
WO WO02/060859 8/2002

OTHER PUBLICATIONS

Shi, et al., Identification of Potential Back-ups For Clinical Candidate CCR3 Antagonist DPC-168, Abstracts of Papers, 234th ACS National Meeting, Boston, MA, United States, Aug. 19-23, 2007 MEDI-382, pp. 1-15.

* cited by examiner

*Primary Examiner*—Charanjit S Aulakh
(74) *Attorney, Agent, or Firm*—Mary K. VanAtten

(57) ABSTRACT

The present application describes modulators of chemokine receptor activity of formula (I):

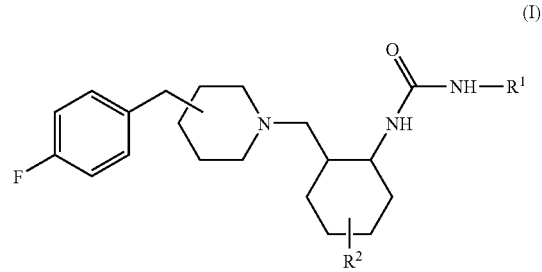

or pharmaceutically acceptable salt forms thereof, useful for the prevention of asthma and other allergic diseases, as well as autoimmune pathologies such as rheumatoid arthritis and atherosclerosis, including methods of preparing and intermediates thereof.

7 Claims, No Drawings

N-UREIDOALKYL-PIPERIDINES AS MODULATORS OF CHEMOKINE RECEPTOR ACTIVITY

CROSS-REFERENCE TO RELATED APPLICATIONS

This application is a continuation of U.S. application Ser. No. 10/865,417, filed Jun. 10, 2004, which claims the priority benefit of U.S. Provisional Application No. 60/478,022, filed Jun. 12, 2003, the disclosure of which are incorporated herein by reference in its entirety.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis, including methods of preparing and intermediates thereof.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1α, RANTES, MCP-1] (Power et al., J. Biol. Chem., 270, 19495-19500 (1995), Luster, New Eng. J. Med., 338, 436-445 (1998)), CCR-5 (or "CKR-5" OR "CC-CKR-5") [MIP-1α, RANTES, MIP-1β] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1β] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)). Two recent reviews of chemokine receptors can be found at (i) A. Zlotnik and O. Yoshi, Immunity 2000, 12, 121-127; and (ii) P. H. Carter, Current Opinion in Chemical Biology 2002, 6, 510-52.

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines, piperizinones and pyrrolidines. These compounds have implicated in the treatment of a variety of disorders.

U.S. Pat. No. 6,444,686, issued Sep. 3, 2002 discloses compounds having the general formula

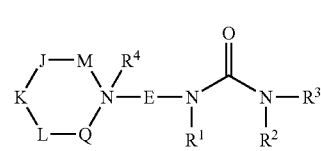

The examples shown in U.S. Pat. No. 6,444,686 are not considered to be part of the present invention The prior art does not discloses nor suggest the unique combination of structural fragments which embody these novel N-ureidoalkyl-piperidines as having activity toward the chemokine receptors.

SUMMARY OF THE INVENTION

Accordingly, one aspect of the present invention is to provide novel agonists or antagonists of CCR-3, or pharmaceutically acceptable salts or prodrugs thereof.

The present invention provides novel agonists or antagonists of CCR-1, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory diseases and allergic disorders comprising administering to a host in need of such treatment a therapeutically effective amount of at least one of the compounds of the present invention or a pharmaceutically acceptable salt or prodrug form thereof.

The present invention provides novel N-ureidoalkyl piperidines for use in therapy.

The present invention provides the use of novel N-ureidoalkyl-piperidines for the manufacture of a medicament for the treatment of allergic disorders.

These and other features, which will become apparent during the following detailed description, have been achieved by the inventors' discovery that compounds of formula (I):

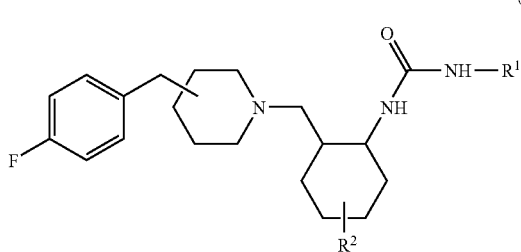

or stereoisomers or pharmaceutically acceptable salts thereof, wherein $R^1$ and $R^2$ are defined below, are effective modulators of chemokine activity.

DETAILED DESCRIPTION OF EMBODIMENTS OF THE PRESENT INVENTION

[1] Thus, in a first embodiment, the present invention provides novel compounds of formula (I):

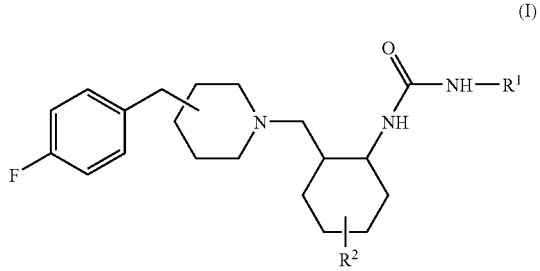

or stereoisomers or pharmaceutically acceptable salts thereof, wherein:

$R^1$ is selected from $C_{1-6}$ alkyl, a $(CH_2)_r$—$C_{3-10}$ carbocyclic residue substituted with 0-5 $R^5$ and a $(CH_2)_r$-5-10 membered heterocyclic system containing 1-4 heteroatoms selected from N, O, and S, substituted with 0-3 $R^5$;

$R^2$, at each occurrence, is selected from $NR^{4a}R^{4a}$, $NR^{4f}C(O)(CHR')_rR^{4b}$, $NR^{4f}C(O)H$, $NR^{4f}S(O)_2(CHR')_rR^{4b}$, and $NR^{4f}C(O)OR^{4b}$;

$R^{4a}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0-5 $R^{4e}$, and a $(CH_2)_r$-5-10 membered heterocyclic system containing 1-4 heteroatoms selected from N, O, and S, substituted with 0-2 $R^{4e}$;

alternatively, two $R^{4a}$ join to form a 5, 6, or 7-membered ring containing from 0-1 additional heteroatoms selected from N and O, the ring containing 0-1 C=O and being substituted with 0-1 $R^f$;

$R^{4b}$, at each occurrence, is selected from $C_{1-6}$ alkyl, $C_{2-8}$ alkenyl, $C_{2-8}$ alkynyl, $C_{1-3}$ perfluoroalkyl, a $(CH_2)_r$—$C_{3-6}$ carbocyclic residue substituted with 0-3 $R^{4e}$, and $(CH_2)_r$-5-6 membered heterocyclic system containing 1-4 heteroatoms selected from N, O, and S, substituted with 0-2 $R^{4e}$;

$R^{4e}$, at each occurrence, is selected from $C_{1-6}$ alkyl, $C_{2-8}$ alkenyl, $C_{2-8}$ alkynyl, $(CH_2)_r$$C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{4f}R^{4f}$, and $(CH_2)_r$phenyl;

$R^{4f}$, at each occurrence, is selected from H, $C_{1-6}$ alkyl, $C_{3-6}$ cycloalkyl, and phenyl;

alternatively, $R^{4b}$ and $R^{4f}$ join to form a 5, 6, or 7-membered ring containing from 0-1 additional heteroatoms selected from N and O, the ring being substituted with 0-1 $R^f$;

$R^f$, at each occurrence, is selected from H, $C_{1-6}$ alkyl, $C_{3-6}$ cycloalkyl, and phenyl;

$R^5$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{5a}R^{5a}$, $(CHR')_rOH$, $(CHR')_rO(CHR')_rR^{5d}$, $(CHR')_rSH$, $(CHR')_rC(O)H$, $(CHR')_rS(CHR')_rR^{5d}$, $(CHR')_rC(O)OH$, $(CHR')_rC(O)(CHR')_rR^{5b}$, $(CHR')_rC(O)NR^{5a}R^{5a}$, $(CHR')_rNR^{5f}C(O)(CHR')_rR^{5b}$, $(CHR')_rC(O)O(CHR')_rR^{5d}$, $(CHR')_rOC(O)(CHR')_rR^{5b}$, $(CHR')_rC(=NR^{5f})NR^{5a}R^{5a}$, $(CHR')_rNHC(=NR^{5f})NR^{5f}R^{5f}$, $(CHR')_rS(O)_p(CHR')_rR^{5b}$, $(CHR')_rS(O)_2NR^{5a}R^{5a}$, $(CHR')_rNR^{5f}S(O)_2(CHR')_rR^{5b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{5e}$, and a $(CH_2)_r$-5-10 membered heterocyclic system containing 1-4 heteroatoms selected from N, O, and S, substituted with 0-2 $R^{5e}$;

$R^{5a}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0-5 $R^{5e}$, and a $(CH_2)_r$-5-10 membered heterocyclic system containing 1-4 heteroatoms selected from N, O, and S, substituted with 0-2 $R^{5e}$;

$R^{5b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-3 $R^{5e}$, and $(CH_2)_r$-5-6 membered heterocyclic system containing 1-4 heteroatoms selected from N, O, and S, substituted with 0-2 $R^{5e}$;

$R^{5d}$, at each occurrence, is selected from $C_{2-8}$ alkenyl, $C_{2-8}$ alkynyl, $C_{1-6}$ alkyl substituted with 0-3 $R^{5e}$, a $(CH_2)_r$—$C_{3-10}$ carbocyclic residue substituted with 0-3 $R^{5e}$, and a $(CH_2)_r$ 5-6 membered heterocyclic system containing 1-4 heteroatoms selected from N, O, and S, substituted with 0-3 $R^{5e}$;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, $C_{3-6}$ cycloalkyl, and phenyl;

R', at each occurrence, is selected from H and $C_{1-6}$ alkyl;

r is selected from 0, 1, 2, 3, 4, and 5; and p is selected from 0, 1, and 2.

[2] In another embodiment, the present invention provides compounds of formula (I), wherein $R^1$ is selected from $C_{1-6}$ alkyl, a $(CH_2)_r$-carbocyclic residue substituted with 0-5 $R^5$, wherein the carbocyclic residue is selected from phenyl, $C_{3-6}$ cycloalkyl, naphthyl, and adamantyl; and a $(CH_2)_r$— heterocyclic system substituted with 0-3 $R^5$, wherein the heterocyclic system is selected from pyridinyl, thiophenyl, furanyl, indazolyl, benzo[1,3]dioxolyl benzothiazolyl, benzimidazolyl, benzothiophenyl, benzofuranyl, benzoxazolyl, benzisoxazolyl, quinolinyl, isoquinolinyl, imidazolyl, indazolyl, indolyl, indolinyl, isoindolyl, isothiadiazolyl, isoxazolyl, 4-oxo-4,5-dihydro-thiazol-2-yl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[3] In another embodiment, the present invention provides compounds of formula (I), wherein $R^2$, at each occurrence, is selected from $NR^{4a}R^{4a}$, $NR^{4f}C(O)R^{4b}$, and $NR^{4f}S(O)_2R^{4b}$;

$R^{4a}$, at each occurrence, are selected from H, $C_{1-6}$ alkyl, $C_{3-6}$ cycloalkyl, and $(CH_2)_r$phenyl substituted with 0-3 $R^{4e}$, and a $(CH_2)_r$-5-6 membered heterocyclic system containing 1-4 heteroatoms selected from N, O, and S, substituted with 0-2 $R^{4e}$;

alternatively, two $R^{4a}$ join to form a 5, 6, or 7-membered ring containing from 0-1 additional heteroatoms selected from N and O, wherein the ring is selected from pyrrolidinyl, piperidinyl, morpholinyl and piperazinyl, the ring containing 0-1 C=O and being substituted with 0-1 $R^f$;

$R^{4b}$, at each occurrence, is selected from H, $C_{1-6}$ alkyl, $C_{3-6}$ cycloalkyl, and $(CH_2)_r$phenyl substituted with 0-3 $R^{4e}$;

$R^{4e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{4f}$, at each occurrence, is selected from H, $C_{3-6}$ cycloalkyl, and $C_{1-5}$ alkyl;

alternatively, $R^{4b}$ and $R^{4f}$ join to form a 5, 6, or 7-membered ring, wherein the ring is selected from 2-piperidinone, the ring being substituted with 0-1 $R^f$;

$R^f$, at each occurrence, is selected from H, methyl, ethyl, propyl, i-propyl, butyl, pentyl, hexyl, cyclopropyl, cyclopentyl, cyclohexyl, and phenyl; and r is selected from 0, 1, and 2.

[4] In another embodiment, the present invention provides compounds of formula (I), wherein $R^1$ is selected from $C_{1-6}$ alkyl selected from methyl, ethyl, propyl, i-propyl, and butyl, a $C_{3-10}$ carbocyclic residue substituted with 0-3 $R^5$, wherein the carbocyclic residue is selected from cyclopropyl, cyclopentyl, cyclohexyl, phenyl, naphthyl and adamantyl, and a $(CH_2)_r$-heterocyclic system substituted with 0-3 $R^5$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indazolyl, indolyl, indolinyl, isoindolyl, isothiadiazolyl, isoxazolyl, 4-oxo-4,5-dihydro-thiazol-2-yl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$, at each occurrence, is selected from $C_{1-8}$ alkyl, $(CH_2)_r$ $C_{3-6}$ cycloalkyl, $CF_3$, Cl, Br, I, F, $(CH_2)_rNR^{5a}R^{5a}$, $NO_2$, CN, OH, $(CHR')_rOR^{5d}$, $(CH_2)_rC(O)R^{5b}$, $(CH_2)_rC(O)OR^{5d}$, $(CH_2)_rC(O)NR^{5a}R^{5a}$, $(CH_2)_rNR^{5f}C(O)R^{5b}$, $(CH_2)_r$ $S(O)_pR^{5b}$, $(CH_2)_rS(O)_2NR^{5a}R^{5a}$, $(CH_2)_rNR^{5f}S(O)_2R^{5b}$, $(CH_2)_r$phenyl substituted with 0-3 $R^{5e}$, and a $(CH_2)_r$-5-6 membered heterocyclic system containing 1-4 heteroatoms selected from N, O, and S, substituted with 0-2 $R^{5e}$;

$R^{5a}$, at each occurrence, are selected from H, $C_{1-6}$ alkyl, $C_{3-6}$ cycloalkyl, and $(CH_2)_r$phenyl substituted with 0-3 $R^{5e}$;

$R^{5b}$, at each occurrence, is selected from H, $C_{1-6}$ alkyl, $C_{3-6}$ cycloalkyl, and $(CH_2)_r$phenyl substituted with 0-3 $R^{5e}$;

$R^{5d}$, at each occurrence, is selected from $C_{1-6}$ alkyl and phenyl;

$R^{5e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{5f}$, at each occurrence, is selected from H, and $C_{1-5}$ alkyl.

[5] In another embodiment, the present invention provides compounds of formula (I), wherein $R^1$ is selected from $C_{1-6}$ alkyl selected from methyl, ethyl, propyl, i-propyl, and butyl, a $C_{3-10}$ carbocyclic residue substituted with 0-2 $R^5$, wherein the carbocyclic residue is selected from cyclopropyl, cyclopentyl, cyclohexyl, phenyl and adamantyl, and a heterocyclic system substituted with 0-3 $R^5$, wherein the heterocyclic system is selected from pyridinyl, indazolyl, benzo[1,3]dioxolyl, benzothiazolyl, benzoxazolyl, benzisoxazolyl, 2,3-dihydroindolyl, indolyl, indazolyl, indolinyl, isoxazolyl, 4-oxo-4,5-dihydro-thiazol-2-yl, pyrrazolyl, pyrimidinyl, 1,2,4-triazolyl, 1,2,3-triazolyl, tetrazolyl, thiadiazolyl, thiazolyl, and oxazolyl; and $R^5$, at each occurrence, is selected from methyl, ethyl, propyl, i-propyl, butyl, s-butyl, i-butyl, t-butyl, pentyl, hexyl, cyclopropyl, $CF_3$, Cl, Br, I, F, CN, OH, $(CHR')_rOR^{5d}$, $C(O)R^{5b}$, $C(O)OR^{5d}$, $C(O)NR^{5a}R^{5a}$, $(CH_2)_rS(O)_pR^{5b}$, $(CH_2)_rNR^{5f}S(O)_2R^{5b}$, $(CH_2)_r$phenyl substituted with 0-3 $R^{5e}$, and a $(CH_2)_r$-5-6 membered heterocyclic system containing 1-4 heteroatoms selected from N, O, and S, substituted with 0-2 $R^{5e}$, wherein the heterocyclic system is selected from tetrazolyl, imidazolyl, pyrimidinyl, pyrrolidinyl, and isoxazolyl;

$R^{5a}$, at each occurrence, are selected from H, methyl, ethyl, propyl, i-propyl, butyl, s-butyl, i-butyl, t-butyl, pentyl, and hexyl;

$R^{5b}$, at each occurrence, is selected from H, methyl, ethyl, propyl, i-propyl, butyl, s-butyl, i-butyl, t-butyl, pentyl, and hexyl;

$R^{5d}$, at each occurrence, is selected from methyl, ethyl, propyl, i-propyl, butyl, s-butyl, i-butyl, t-butyl, pentyl, and hexyl; and $R^{5e}$, at each occurrence, is selected from methyl, ethyl, propyl, i-propyl, butyl, s-butyl, i-butyl, t-butyl, pentyl, and hexyl.

[6] In another embodiment, the present invention provides compounds of formula (I), wherein $R^2$, at each occurrence, is selected from $NR^{4a}R^{4a}$, $NR^{4f}C(O)R^{4b}$, and $NR^{4f}S(O)_2R^{4b}$;

$R^{4a}$, at each occurrence, are selected from H, methyl, ethyl, propyl, i-propyl, butyl, s-butyl, i-butyl, t-butyl, pentyl, hexyl, cyclopropyl, cyclobutyl, cyclopentyl, and cyclohexyl;

alternatively, two $R^{4a}$ join to form a 5, 6, or 7-membered ring containing from 0-1 additional heteroatoms selected from N and O, wherein the ring is selected from pyrrolidinyl, piperidinyl, morpholinyl and piperazinyl, the ring being substituted with 0-1 $R^f$;

$R^{4b}$, at each occurrence, is selected from H, methyl, ethyl, propyl, i-propyl, butyl, s-butyl, i-butyl, t-butyl, pentyl, and hexyl;

$R^{4f}$, at each occurrence, is selected from H, methyl, ethyl, propyl, i-propyl, butyl, s-butyl, i-butyl, t butyl, pentyl, hexyl, cyclopropyl, cyclobutyl, cyclopentyl, cyclopropyl, cyclobutyl, cyclopentyl and cyclohexyl;

alternatively, $R^{4b}$ and $R^{4f}$ join to form a 5, 6, or 7-membered ring, wherein the ring is selected from 2-piperidinone, the ring being substituted with 0-1 $R^f$; and $R^f$, at each occurrence, is selected from methyl, ethyl, propyl, and i-propyl.

[7] In another embodiment, the present invention provides compounds of formula (I), wherein the compound is selected from the compounds of Table 1 and Table 2 and the Examples.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides pharmaceutical composition comprising a pharmaceutically acceptable carrier and a therapeutically effective amount of a compound of the present invention or a pharmaceutically acceptable salt thereof.

In another embodiment, the present invention provides a method of modulation of chemokine receptor activity which comprises contacting a CCR3 receptor with an effective inhibitory amount of the compound.

In another embodiment, the present invention provides a method of modulation of chemokine receptor activity which comprises contacting a CCR1 receptor with an effective inhibitory amount of the compound.

In another embodiment, the present invention provides a method of modulation of chemokine receptor activity wherein inhibiting chemokine receptor activity comprises inhibiting CCR-1 activity.

In another embodiment, the present invention provides a method for treating inflammatory disorders comprising administering to a patient in need thereof a therapeutically effective amount of a compound of the present invention, or a pharmaceutically acceptable salt thereof.

In another embodiment, the present invention provides a method for treating disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the present invention provides a method for treating disorders selected from asthma, allergic rhinitis, atopic dermatitis, and inflammatory bowel diseases.

In another embodiment, the present invention provides a method for treating asthma.

In another embodiment, the present invention provides a method for treating allergic rhinitis.

In another embodiment, the present invention provides a method for treating atopic dermatitis.

In another embodiment, the present invention provides a method for treating inflammatory bowel diseases.

In another embodiment, the present invention provides novel N-ureidoalkyl-piperidines compounds for use in therapy.

In another embodiment, the present invention provides the use of novel N-ureidoalkyl-piperidines compounds for the manufacture of a medicament for the treatment of HIV infection.

In another embodiment, the present invention provides a compound of formula (Ia):

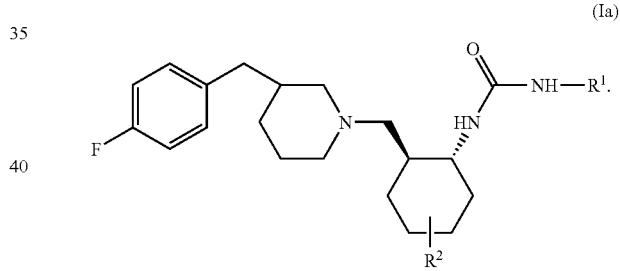

(Ia)

In another embodiment, the present invention provides a compound of formula (Ib):

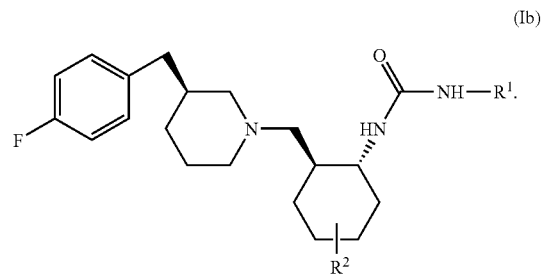

(Ib)

In another embodiment, the present invention provides a compound of formula (Ic):

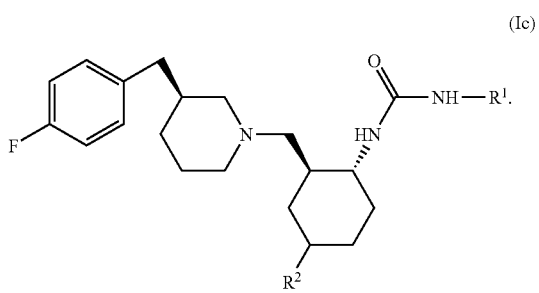

In another embodiment, the present invention provides a compound of formula (Id):

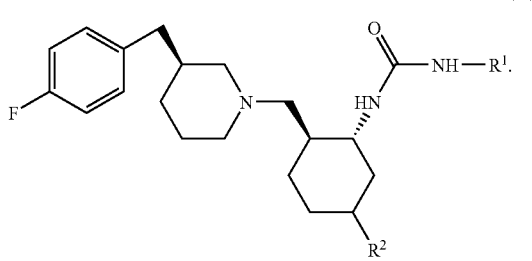

In another embodiment, $R^1$ is selected from $C_{1-6}$ alkyl, a $C_{3-10}$ carbocyclic residue substituted with 0-3 $R^5$, wherein the carbocyclic residue is selected from cyclopropyl, cyclopentyl, cyclohexyl, phenyl, naphthyl and adamantyl, and a $(CH_2)_r$-heterocyclic system substituted with 0-3 $R^5$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^1$ is selected from $C_{1-6}$ alkyl selected from methyl, ethyl, propyl, i-propyl, and butyl, a $C_{3-10}$ carbocyclic residue substituted with 0-2 $R^5$, wherein the carbocyclic residue is selected from cyclopropyl, cyclopentyl, cyclohexyl, phenyl and adamantyl, and a heterocyclic system substituted with 0-3 $R^5$, wherein the heterocyclic system is selected from pyridinyl, indazolyl, benzo[1,3]dioxolyl, benzothiazolyl, benzoxazolyl, benzisoxazolyl, 2,3-dihydroindolyl, indolyl, indazolyl, indolinyl, isoxazolyl, 4-oxo-4,5-dihydro-thiazol-2-yl, pyrrazolyl, pyrimidinyl, 1,2,4-triazolyl, 1,2,3-triazolyl, tetrazolyl, thiadiazolyl, thiazolyl, and oxazolyl.

In another embodiment, the present invention is directed to a process of preparing a compound of formula (IV),

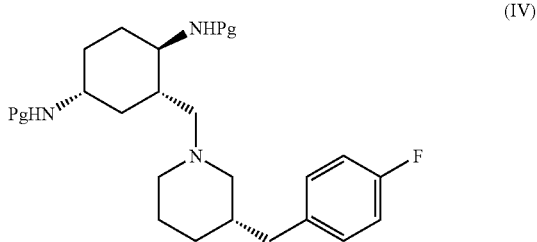

or salt or stereoisomer thereof: wherein
Pg, at each occurrence, is independently selected from an amine protecting group;
comprising the steps of reacting a compound of Formula II,

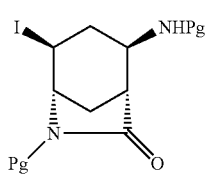

with a deiodinator and reducing agent to give a compound of Formula III;

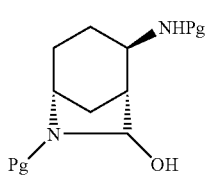

reacting the compound of formula (III) with an amine of formula (IIa) using reductive amination to give the compound of formula (II)

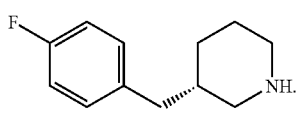

In another embodiment, the present invention is directed to a process of preparing a compound of formula (IV),

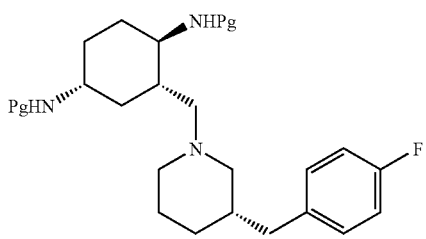

or salt or stereoisomer thereof: wherein

Pg, at each occurrence, is independently selected from an amine protecting group;
comprising the steps of reacting a compound of Formula III

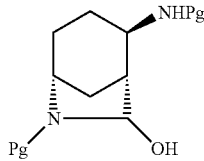

(III)

with an amine of formula (IIa) using reductive amination to give the compound of formula (II)

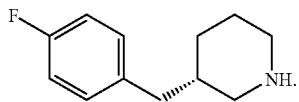

(IIa)

In another embodiment, the present invention is directed compound of Formula (III)

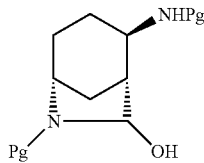

(III)

or salt or stereoisomer thereof, wherein

Pg, at each occurrence, is independently selected from an amine protecting group.

In another embodiment, the present invention is directed to a compound of Formula (V)

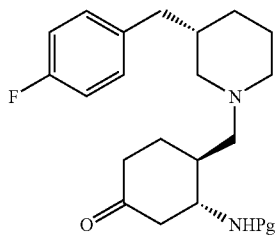

(V)

wherein Pg is an amine protecting group.

In another embodiment, the present invention is directed to a compound of Formula (V), wherein Pg is benzyloxycarbonyl (Cbz).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^5$) occurs more than one time in any constituent or formula for a compound, its definition at each occurrence is independent of its definition at every other occurrence. Thus, for example, if a group is shown to be substituted with 0-2 $R^5$, then said group may optionally be substituted with up to two $R^5$ groups and $R^5$ at each occurrence is selected independently from the definition of $R^5$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl, $C_{3-6}$ cycloalkyl, is intended to include $C_3$, $C_4$, $C_5$, and $C_6$ cycloalkyl groups.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. The "amine protecting group" should be compatible with other reaction conditions. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: 1) acyl types such as formyl, trifluoroacetyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; and 4) cyclic alkyl carbamate types such as cyclopentyloxycarbonyl and adamantyloxycarbonyl.

Amine protecting groups may include, but are not limited to the following: 2,7-di-t-butyl-[9-(10,10-dioxo-10,10,10,10-tetrahydrothioxanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; or 2-furanylmethyloxycarbonyl.

A suitable selective "deiodinator", also referred to as a reducing agent, is a reagent or combination of reagents which will selectively reduce (reducing agent) the W or I group in the compound of Formula (II) to a hydrogen without altering the character of the other substitutents. Suitable selective deiodinators include, but are not limited to, tris-(trimethylsilyl)silane, zinc metal, tributyltin hydride and catalytic versions, see Gregory Fu, Org. Syn. (2002), 78, 239-248 which is hereby incorporated by reference, and AIBN (2,2'-Azobisisobutyronitrile).

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are envisioned for this invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1999).

U.S. Pat. No. 6,444,686 describes the synthesis of CCR-3 inhibitors. The synthesis of these compounds is hereby incorporated by reference.

Compounds of this invention could be synthesized using the procedures summarized in Schemes 1-5 below. The commercially available 1,4-cyclohexanedione monoethylene ketal is treated with NaH and diethylcarbonate to give the keto ester 1 as shown in Scheme 1. The keto ester 1 is then condensed with the commercially available chiral amine R-(+)-α-methylbenzyl amine to give the ene-amine 2. Reduction of the ene-amine 2 with sodium triacetoxyborohydride (STAB) or hydrogenation at 250 psi over $PtO_2$ gives the cis β-amino ester 3. The cis β-amino ester is isomerized to the trans isomer 4 with sodium tert-butoxide in THF. The ester is reduced with lithium aluminum hydride (LAH) to give the alcohol 5. The benzyl amine of 5 is hydrogenated over $Pd(OH)_2$ on carbon at 50 psi of hydrogen to give the amino alcohol 6. The amino group of 6 is protected as the benzyl carbamate by treatment with benzyl chloroformate to give the CBZ protected amine 7 as shown in Scheme 1. Alternatively, other compatible amine protecting groups may be used in place of CBZ to protect the amine. Swern oxidation of 7 provides the aldehyde 8 as shown in Scheme 2. Reductive amination of the aldehyde with 3S-(4-F-benzyl)piperidine gives the corresponding piperidine 9. The cyclic ketal of 9 is removed by treatment with aqueous HCl to provide the ketone 10 as summarized in Scheme 2. The ketone 10 can be reductively aminated to give a mixture of R and S isomers. The ratio of isomers that is obtained depends on the method used as summarized in Scheme 3 using methylamine as the example. Using STAB as the reducing agents gives mainly the S isomer when the reaction is run in dilute solutions and approximately a 1:1 ratio of R/S amine isomers under more concentrated reaction conditions. Using NaCNBH$_3$ as the reducing agent gives a 1:1 ratio of isomers, whereas, the use of titanium isopropoxide and NaBH$_4$ generally gives the R isomer, 11, as the major product as shown in Scheme 3. The amine 11 is reacted with acetic anhydride to give the amide 12. The primary amine protecting group of 12 is removed using catalytic hydrogenation (10% Pd/C) at 55 psi in methanol to give the free amine 13 as shown in Scheme 4. The amine is treated with the phenyl carbamate in THF at room temperature to give the desired urea 14 in good yields. The ketone intermediate 10 can undergo reductive amination with a wide variety of secondary amines (HNR$^a$R$^b$, Scheme 5) to give the tertiary amines 15. Some of the secondary amine that were used includes dimethylamine, piperidine, morpholine, and piperazinone. The tertiary amines 15, are then hydrogenated to remove the CBZ protecting group and the resulting free amine can be treated with carbamates or isocyanates to give a variety of ureas 16 as shown in Scheme 5. Alternatively, the ketone intermediate 10 can be reductively aminated with ammonia or primary amines (NH$_2$R$^a$, Scheme 5) to give the corresponding primary or secondary amine 17. This primary amine can then be treated with Boc$_2$O or methanesulfonyl chlorides to give 18 (R$^c$=Boc or Mesyl) as shown in Scheme 5. The amines 18, are then hydrogenated to remove the CBZ protecting group and the resulting free amine can be treated with carbamates or isocyanates to give a variety of ureas 19. When R$^c$ of 19 is a Boc group, this is removed by treatment with trifluoroacetic acid to give the free amine (R$^c$=H). A detailed example of the procedures used is given below.

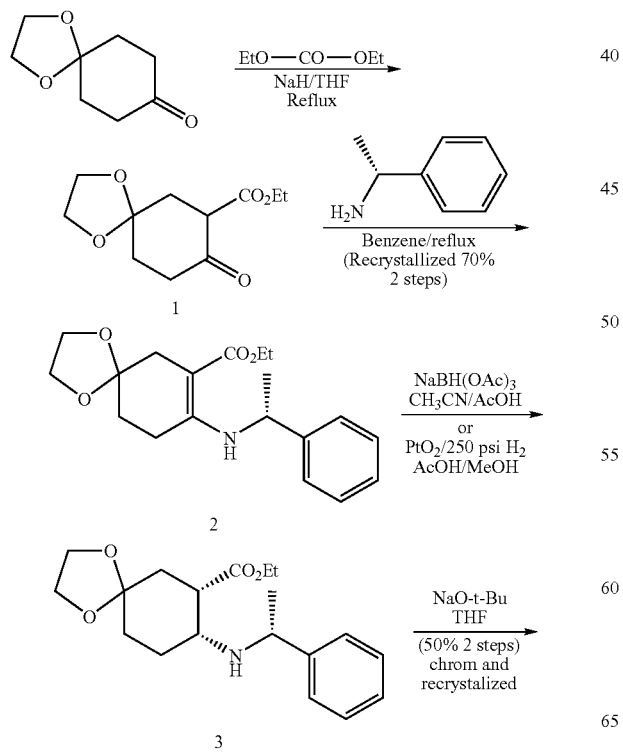

Scheme 1.

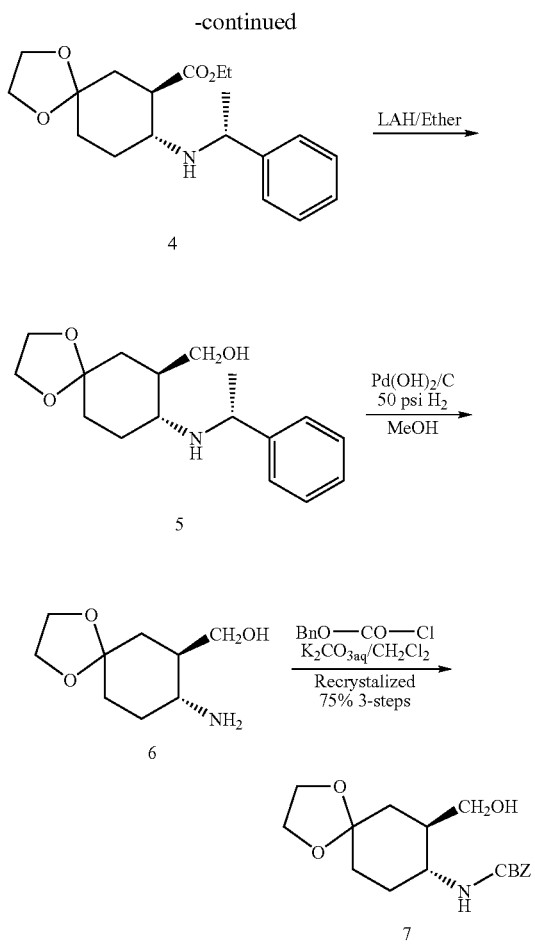

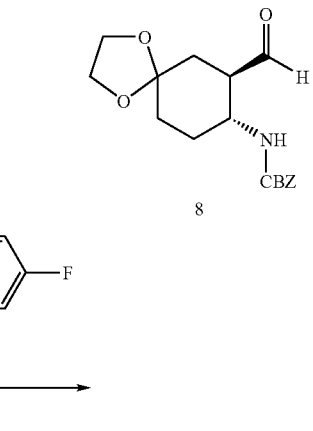

Scheme 2.

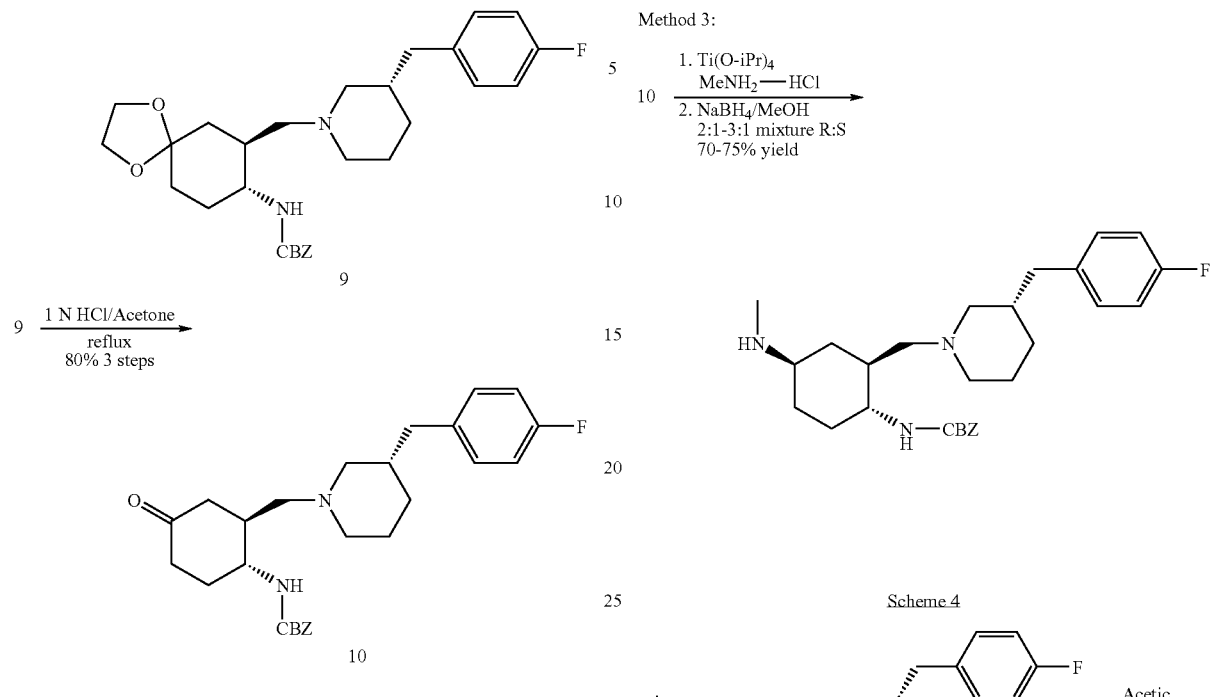
Scheme 3
Method 1:
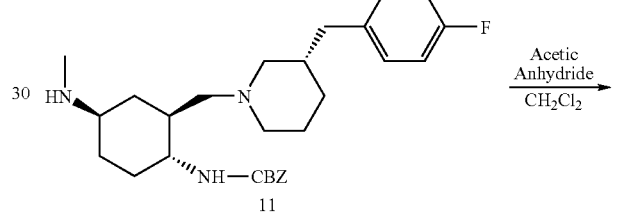
Method 2:
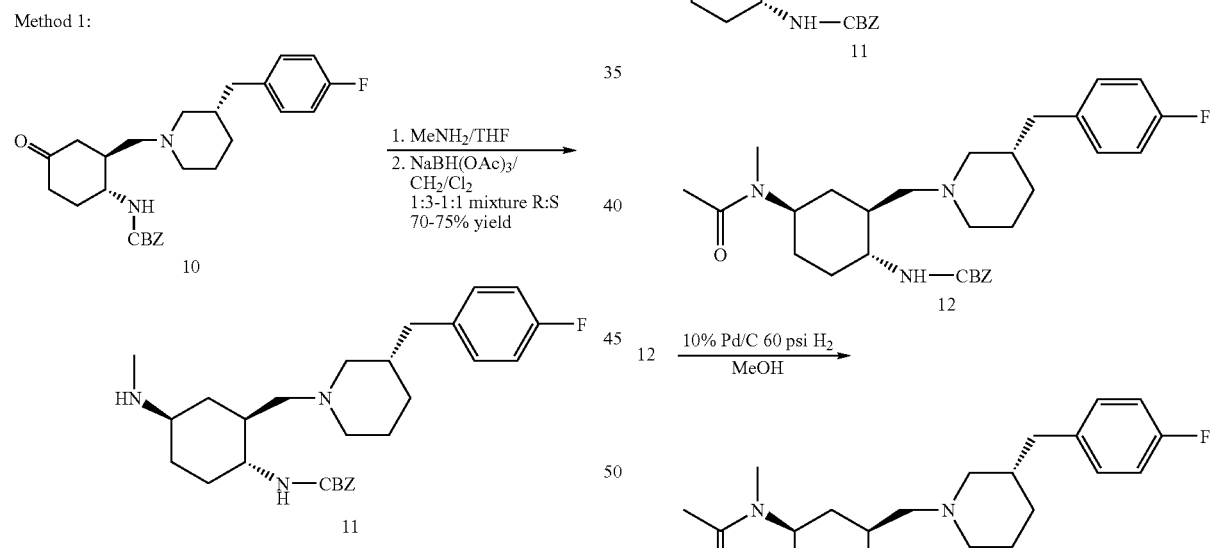
Scheme 4
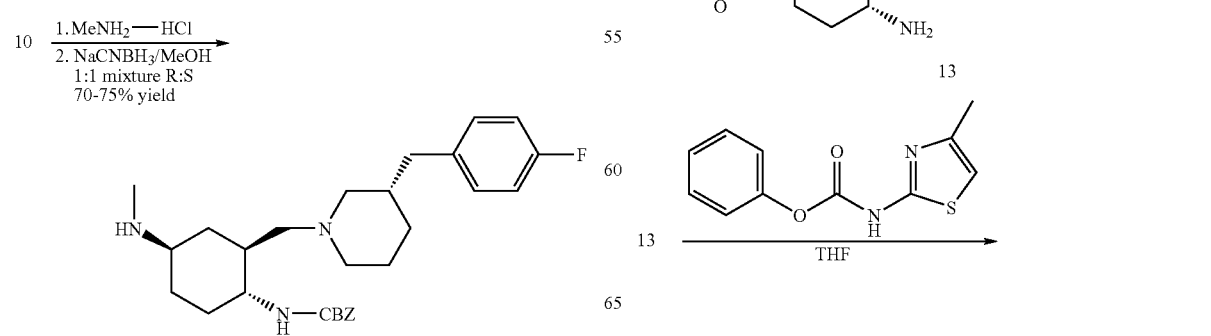

-continued
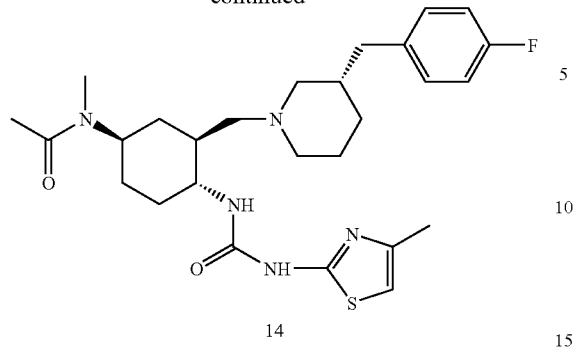
14
Scheme 5
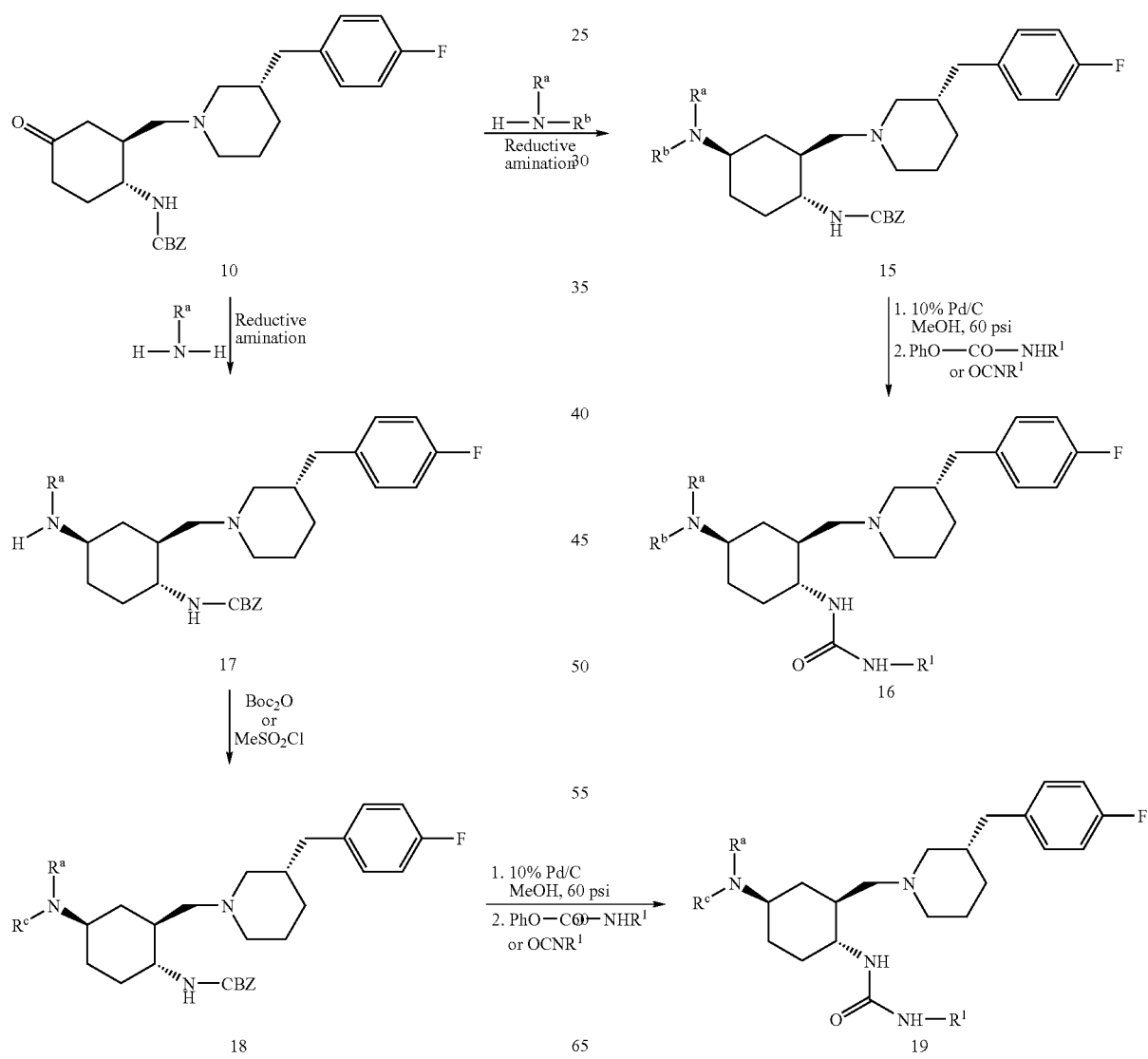

EXAMPLES

The compounds of this invention and their preparation can be understood further by the following working examples. These examples are meant to be illustrative of the present invention, and are not to be taken as limiting thereof.

Example 1

N-{(3S,4R)-3-[3S-(4-Fluorobenzyl)-piperidin-1-ylmethyl]-4-[3-(4-methyl-thiazol-2-yl)-ureido]-(R)-cyclohexyl}-N-methyl-acetamide

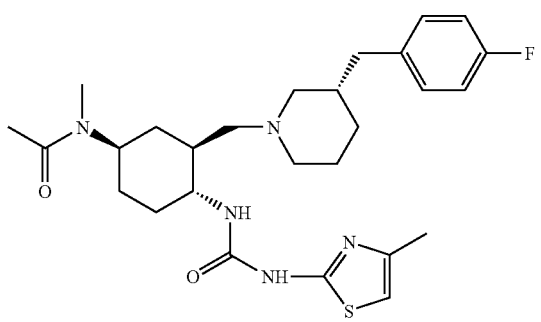

Step a.
8-Oxo-1,4-dioxa-spiro[4.5]decane-7-carboxylic acid ethyl ester (1a)

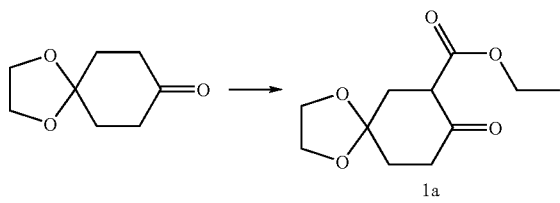

Into a 2-L 3-neck flask was added NaH (60% dispersion; 60 g, 1.56 mol) and washed with 700 ml of hexane (2×), suspended in 1 L of THF and treated with diethylcarbonate (150 g, 1.25 mol). The suspension was heated to reflux and treated drop-wise with a solution of ketone (80.0 g 0.51 mol) in THF (300 ml). After the addition was complete the suspension was heated to reflux for an additional 4 hours. The mixture was cooled in an ice bath to 0° C. and then poured, while vigorously stirring, into a mixture of ice (1.5 L), water (100 ml) and acetic acid (150 ml). The resulting mixture was extracted with hexane (3 L total) and the extracts washed with water and brine. The hexane extract was dried over $Na_2SO_4$, filtered and concentrated to give the ester product 1a as a pale yellow oil. This was used without further purification. $^1$H NMR (300 MHz, $CDCl_3$) δ(TMS): 12.25 (s, 1H), 4.20 (q, J=7 Hz, 2H), 4.06-3.96 (m, 4H), 2.53-2.48 (m, 4H), 1.84 (t, J=6.6 Hz, 2H), 1.29 (t, J=7 Hz, 3H).

Step b: 8-(R-1-Phenyl-ethylamino)-1,4-dioxa-spiro[4.5]dec-7-ene-7-carboxylic acid ethyl ester (1b)

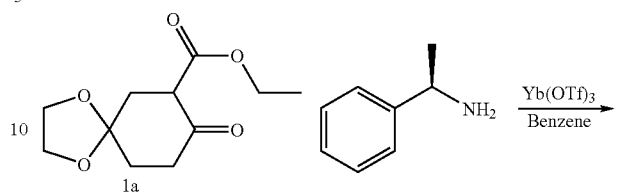

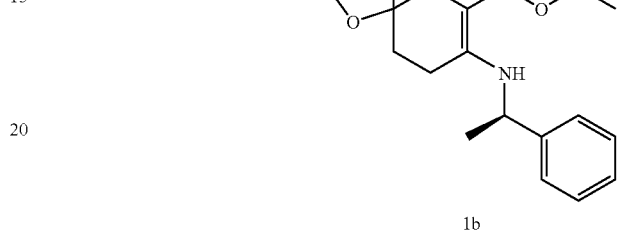

A solution of crude ester 1a in benzene (500 mL) was treated with (R)-1-Phenyl-ethylamine (61.8 g, 0.51 mol) and $Yb(OTf)_3$ catalyst (0.8 g) and heated to reflux for 2-3 hours with the removal of water with a Dean-Stark trap. The resulting solution is concentrated on a rotary evaporator to give a yellow solid. This is titurated with 300 mL of 20% isopropyl alcohol in hexane to give a nearly white solid. The solid is recrystallized from 300 ml of hexane to give 108 grams of crystalline ene-amine 1b. $^1$H NMR (300 MHz, $CDCl_3$) δ(TMS): 9.41 (d, J=7.4 Hz, 1H), 7.35-7.20 (m, 5H), 4.64-4.58 (m, 1H), 4.14 (q, J=7 Hz, 2H), 4.02-3.88 (m, 4H), 2.57-2.49 (m, 3H), 2.25-2.15 (m, 1H), 1.72-1.65 (m, 2H), 1.48 (d, J=7.4 Hz, 3H), 1.28 (t, J=7 Hz, 3H).

Step c: (7S,8R)-8-(R-1-Phenyl-ethylamino)-1,4-dioxa-spiro[4.5]decane-7-carboxylic acid ethyl ester (3)

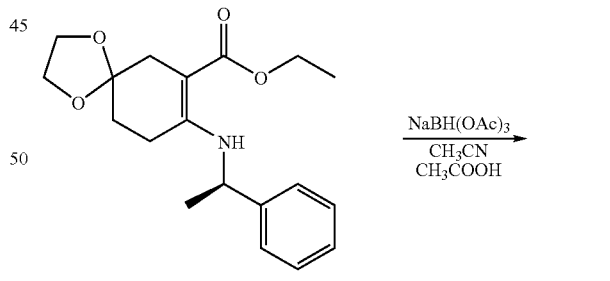

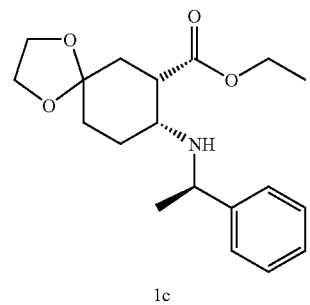

A solution of ene-amine 1b (380 g, 1.14 mol) in 700 ml of acetonitrile and 350 ml of acetic acid is cooled in an ice bath and treated with NaBH(OAc)$_3$ (360 g, 1.71 mol) powder and stirred for 30 minutes, removed ice bath, and stirred overnight at room temperature. The solution is concentrated on a rotary evaporator and the residue dissolved in CH$_2$Cl$_2$ and concentrated on a rotary evaporator a couple of times to removed as much acetic acid as possible. The residue is dissolved in 2 L of CH$_2$Cl$_2$ and divided in 2 equal parts. While cooling in an ice bath and by adding ice into the solution, each part of the solution was neutralized by the slow addition of 50% NaOH (205 g) while vigorously stirring. The resulting mixture was separated and the organic phase washed with water and brine, dried over Na$_2$SO$_4$, filtered and concentrated on a rotary evaporator to give 380 g of the cis ester amine as a thick oil. The crude product was used without further purification.

$^1$H NMR (300 MHz, CDCl$_3$) δ(TMS): 7.34-7.21 (m, 5H), 4.18 (q, J=7 Hz, 2H), 3.95-3.88 (m, 4H), 3.73 (q, J=7 Hz, 1H), 3.14 (m, 1H), 2.81 (m, 1H), 2.08 (m, 1H), 1.80-1.38 (m, 6H), 1.32-1.25 (m, 6H).

Step d: (7R,8R)-8-(R-1-Phenyl-ethylamino)-1,4-dioxa-spiro[4.5]decane-7-carboxylic acid ethyl ester (4)

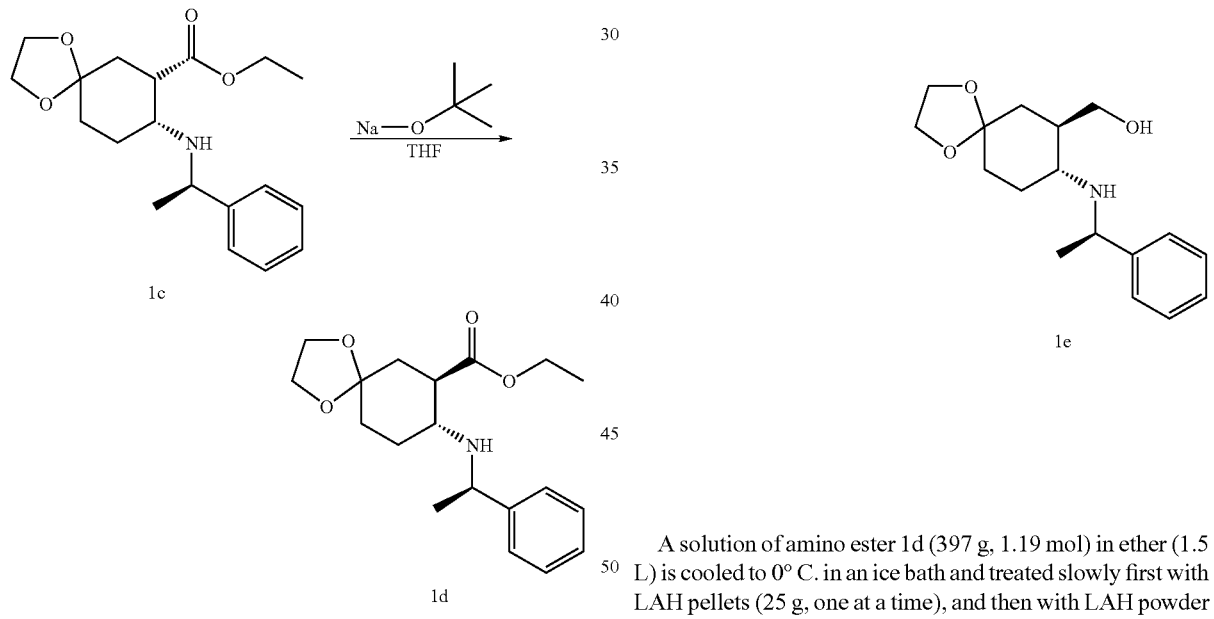

A solution of sodium t-butoxide (185 g, 1.92 mol) in THF (1 L) was prepared and cooled to 0° C. and added to a solution of the crude cis amino ester 1c while cooling in ice bath. After mixing, the ice bath is removed and the mixture is stirred at room temperature for 4 hours. The solution is then poured into a mixture of cold 1 N HCl (2 L) and Ethyl acetate (2 L) while stirring vigorously. The pH is adjusted to slightly basic with 1 N NaOH and the organic layer separated. The aqueous layer is extracted with ethyl acetate and the combine ethyl acetate extracts are washed with water, brine, and then concentrated on a rotary evaporator to give 380 grams of thick oil. This was chromatographed in two equal portions on 2.5 Kg of silica gel eluting with 50% ethyl acetate/hexane to give a total of 280 g of mostly trans isomer as an oil which slowly solidified on standing. This was further purified by recrystallization from hexane after cooling in freezer to give 210 grams of 1d as a crystalline solid.

$^1$H NMR (300 MHz, CDCl$_3$) δ(TMS): 7.30-7.21 (m, 5H), 4.22-4.14 (m, 2H), 3.93-3.87 (m, 4H), 3.80 (q, J=7 Hz, 1H), 2.82-2.77 (m, 1H), 2.56-2.47 (m, 1H), 1.86-1.32 (m, 7H), 1.32-1.25 (m, 6H).

Step e: [(7R,8R)-8-(R-1-Phenyl-ethylamino)-1,4-dioxa-spiro[45]dec-7-yl]-methanol A solution of amino ester 1d (397 g, 1.19 mol) in ether (1.5 L) is cooled to 0° C. in an ice bath and treated slowly first with LAH pellets (25 g, one at a time), and then with LAH powder (41 g, portion-wise; total 66 g, 1.73 mol). After the addition is complete the mixture is stirred for an additional 45 minutes and then quenched by drop-wise addition of 66 ml of water followed by 264 ml of 1 N NaOH (caution: vigorous foaming). The resultant suspension is stirred in the ice bath for 1-2 hours to give a granular white suspension, which is filtered on a Buchner funnel. The solid is washed with ether and the combine ether filtrates are concentrated to give 346 g of the alcohol 1e as a colorless syrup. This is used without further purification.

$^1$H NMR (300 MHz, CDCl$_3$) δ(TMS): 7.35-7.25 (m, 5H), 3.95-3.90 (m, 4H), 3.60-3.47 (m, 3H), 2.61-2.48 (m, 1H), 2.12-2.04 (m, 1H), 1.87-1.42 (m, 4H), 1.39 (d, J=6 Hz, 3H), 1.25-1.16 (m, 2H).

Step f: ((7R,8R)-8-Amino-1,4-dioxa-spiro[4.5]dec-7-yl)-methanol

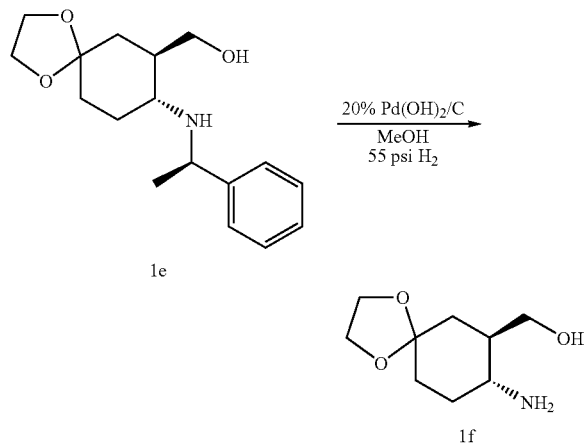

A solution of crude amino alcohol 1e (347 g, 1.19 mol) in 500 ml of MeOH was treated with 50 g of 20% Pd(OH)$_2$/C and hydrogenated overnight at 55 psi. The mixture was filtered through Celite and concentrated on a rotary evaporator to give the amino alcohol 1f as a syrup. This was used without further purification.

$^1$H NMR (300 MHz, CDCl$_3$) δ(TMS): 3.96 (bs, 4H), 3.58 (d, J=7 Hz, 2H), 2.94 (bs, 3H), 2.57 (m, 1H), 1.84-1.48 (m, 6H), 1.20 (t, J=13 Hz, 1H).

Step g: ((7R,8R)-7-Hydroxymethyl-1,4-dioxa-spiro[4.5]dec-8-yl)-carbamic acid benzyl ester

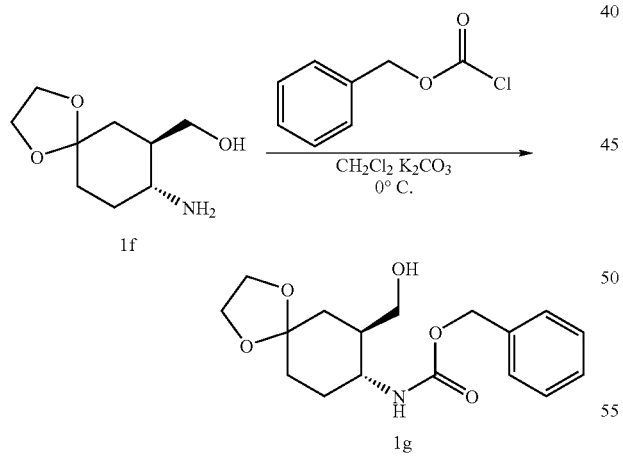

A solution of crude amino alcohol 1f (223 g, 1.19 mol) in 1 L of CH$_2$Cl$_2$ was treated with a 1 L aqueous solution of K$_2$CO$_3$ (200 g, 1.45 mol) and cooled in a ice bath. The mixture is stirred vigorously while benzyl chloroformate (225 g, 1.3 mol) is added slowly. After the addition is complete the mixture is stirred an additional 30 min. The organic layer is separated and washed with water, brine and concentrated to give 390 g of crude product. This is recrystallized from hexane to give 270 g of N-CBZ amino alcohol 1g.

$^1$H NMR (300 MHz, CDCl$_3$) δ(TMS): 7.36-7.32 (s, 5H), 5.11 (s, 2H), 4.82 (d, J=8 Hz, 1H), 3.96-3.88 (m, 4H), 3.72 (m, 1H), 3.53 (m, 1H), 3.32 (m, 2H), 1.95-1.52 (m, 7H).

Step h: ((7R,8R)-7-Formyl-1,4-dioxa-spiro[4.5]dec-8-yl)-carbamic acid benzyl ester

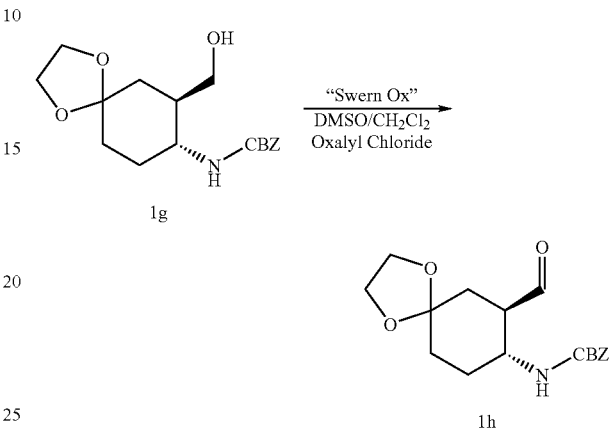

A solution of DMSO (100 g, 1.2 mol) in 450 ml of methylene chloride was cooled to −78° C. (dry ice-acetone bath) and treated drop-wise with oxalyl chloride (126 g, 1.0 mol). After the addition was complete and solution was stirred for 30 minutes and then treated drop-wise with a solution of alcohol 1g (96 g, 0.29 ml) in 200 ml of methylene chloride from an addition funnel. After the addition was complete and solution was stirred for 40 minutes and then treated with 250 ml of triethylamine (182 g, 1.8 mol) and stirred for 30 minutes before removing the cooling bath and stirring at room temperature for 1 hour. The mixture was quench with 1 L of saturated sodium bicarbonate and the organic layer was separated and washed successively with water and brine, and then dried over Na$_2$SO$_4$. The drying is filtered and the solvent removed on a rotary evaporator to give 96 grams of crude aldehyde 1h as a light yellow solid with was used without further purification.

$^1$H NMR (300 MHz, CDCl$_3$) δ(TMS): 9.61 (d, 1.5 hz, 1H), 7.36-7.27 (m, 5H), 5.07 (m, 2H), 4.83 (bd, J=7 Hz, 1H), 3.95 (bs, 4H), 2.54 (m, 1H), 2.05 (m, 1H), 1.89-1.57 (m, 6H).

Step i: {((7S,8R)-7-[3S-(4-Fluorobenzyl)-piperidin-1-ylmethyl]-1,4-dioxa-spiro[4.5]dec-8-yl}-carbamic acid benzyl ester

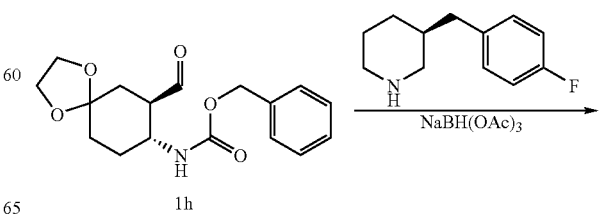

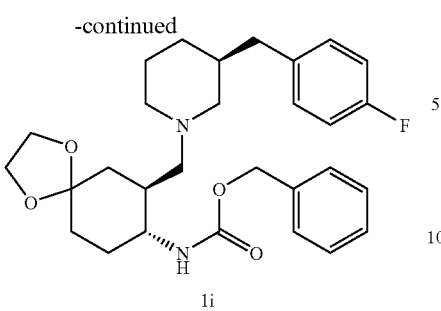
1i

A solution of crude aldehyde 1h (46.8 g, 0.146 mol) and 3S-(4-fluorobenzyl)piperidine (33.0 g, 0.171 mol) in 700 ml of methylene chloride was cooled in an ice bath and treated with NaBH(OAc)₃ (46.41 g, 0.219 mol). The resulting mixture was then stirred at room temperature overnight. Reaction was quenched with 1 N NaOH (2 L) and stirred at room temperature for 1 hour. The organic layer was separated and washed with water and brine. The solvent is removed on a rotary evaporator to give 73 g of crude amine 1i as an oil which was used without further purification.

¹H NMR (300 MHz, CDCl₃) δ(TMS): 7.86 (s, 1H), 7.36-7.29 (m, 5H), 6.87 (d, J=8 Hz, 4H), 5.08 (m, 2H), 3.92-3.89 (m, 4H), 3.11 (m, 1H), 2.83 (m, 1H), 2.60-2.29 (m, 4H), 2.10-1.20 (m, 16H), 0.90 (m, 1H). MS ESI (M+H)⁺=497.3.

Step j: {(1R,2S)-2-[3S-(4-Fluorobenzyl)-piperidin-1-ylmethyl]-4-oxo-cyclohexyl}-carbamic acid benzyl ester

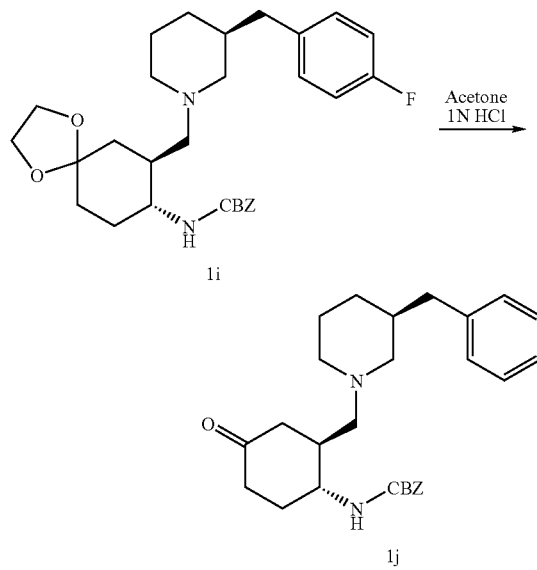

A solution of crude ketal 1i (73 g, 0.146 mol) in 300 ml acetone was treated with 1 N HCl (200 ml) and heated to reflux for 4 hours. Most of the acetone was removed on a rotary evaporator and the aqueous residue was made basic with 1 N NaOH. The resulting suspension was extracted into CH₂Cl₂ and the organic extract was washed with water and brine. The solvent was removed on a rotary evaporator and the residue chromatographed on silica gel (50% ethyl acetate/hexane) to give 55 g of ketone 1j as a thick oil.

¹H NMR (300 MHz, CDCl₃) δ(TMS): 7.98 (bs, 1H), 7.37-7.26 (m, 5H), 6.88 (m, 4H), 5.11 (m, 2H), 3.54 (m, 1H), 2.87-1.39 (m, 20H), 0.90 (m, 1H).

Step k: {(1R,2S)-2-[3S-(4-Fluorobenzyl)-piperidin-1-ylmethyl]-4-methylamino-cyclohexyl}-carbamic acid benzyl ester Method 1.

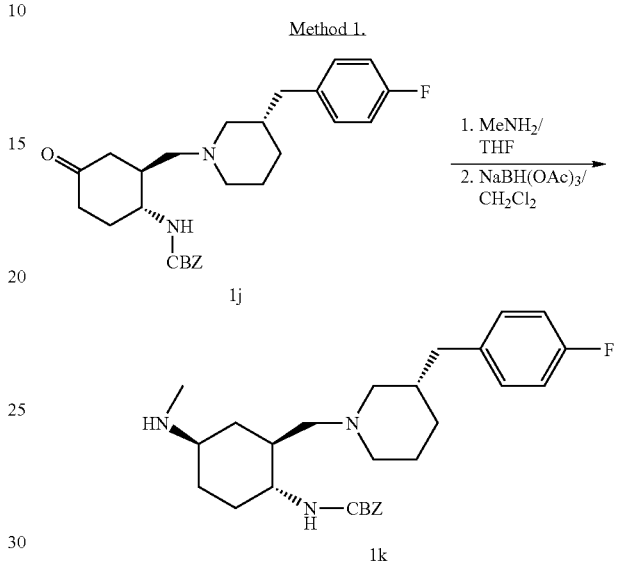

A solution of ketone (1.67 g, 3.7 mol) in CH₂Cl₂ (25 ml) is treated with 2 M THF solution of methylamine (2 ml, 4 mmol) and NaBH(OAc)₃ (1.17 g, 5.5 mmol) and stirred at room temperature for 3 hours. Reaction was quenched with 1 N NaOH (25 ml) and stirred at room temperature for 1 hour. The organic layer was separated and washed with water and brine. The solvent is removed on a rotary evaporator and the residue was chromatographed on silica gel (0.2:1.8:98-0.7:6.3:93 NH₄OH/MeOH/CH₂Cl₂) to give two isomers.

S isomer eluted first to give 0.8 g as oil.

¹H NMR (300 MHz, CDCl₃) δ(TMS): 7.39-7.25 (m, 6H), 6.91-6.80 (m, 4H), 5.08 (m, 2H), 3.15 (m, 1H), 2.81 (m, 1H), 2.72 (m, 1H), 2.56 (m, 1H), 2.46-2.22 (m, 3H), 2.35 (s, 3H), 2.21-1.98 (m, 2H), 1.90-1.25 (m, 12H), 1.19 (m, 1H), 0.90 (m, 1H).

The R isomer 1k eluted second to give 0.4 g of a white solid.

¹H NMR (300 MHz, CDCl₃) δ(TMS): 7.86 (bs, 1H), 7.37-7.27 (m, 5H), 6.95-6.80 (m, 4H), 5.08 (m, 2H), 3.06 (m, 1H), 2.80 (m, 1H), 2.60-2.50 (m, 6H), 2.41 (s, 3H), 2.08 (m, 1H), 1.95-0.78 (m, 14H).

Method 2:

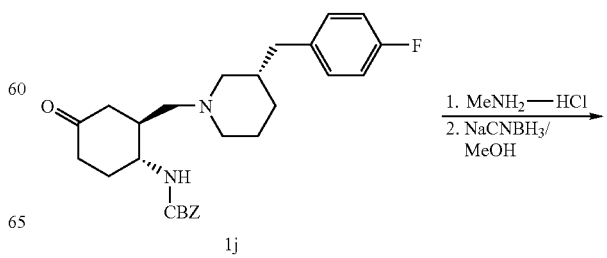

-continued

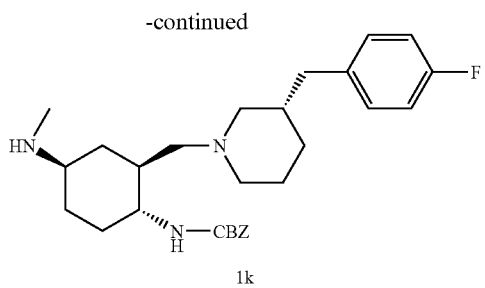

1k

A solution of ketone (4.4 g, 9.7 mmol) in methanol (100 ml) was treated with methylamine hydrochloride (6.75 g, 100 mmol) and stirred until all the salt dissolved. The solution was treated with NaCNBH₃ and stirred at room temperature overnight. The solution was concentrated on a rotary evaporator and the residue treated with 1 N NaOH and extracted into $CH_2Cl_2$, and washed with water and brine. The solvent is removed on a rotary evaporator and the residue was chromatographed on silica gel (0.2:1.8:98-0.7:6.3:93 NH₄H/MeOH/$CH_2Cl_2$) to give two isomers. The S isomer eluted first to give 1.3 g as oil and the R isomer eluted second to give 1.3 g of 1k as a white solid.

Method 3.

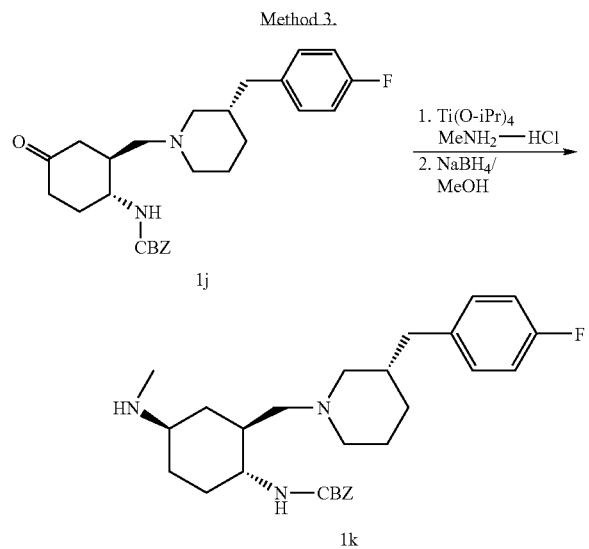

Ketone 1j (17.0 g, 37.6 mmol) was dissolved in titanium (IV) isopropoxide (23 ml, 21.5 g, 75.6 mol) and treated with methylamine hydrochloride (5.1 g, 75.5 mmol). Enough methanol was added to the mixture to dissolve the salt after stirring for several minutes. The resulting solution was stirred at room temperature for 5 hours. The solution was diluted with 50 ml of methanol and treated very slowly with NaBH₄ caplets (2.85 g, 75 mmol) over a period of 2 hours. [Caution: vigorous foaming occurs.] The solution was stirred overnight at room temperature. The solution was quenched with a 0.2 N NaOH and the resulting slurry was diluted with 1 L of $CH_2Cl_2$ and shaken thoroughly in a separatory funnel. The resulting emulsion is filtered through Celite and the solid cake washed two times with $CH_2Cl_2$. The combined filtrates were concentrated on a rotary evaporator to give 17 grams of brown oil which was chromatographed on 1.5 Kg of silica gel (elution with 1:9:90 NH₄OH/MeOH/$CH_2Cl_2$) to give two isomers. The S isomer eluted first to give 4.0 g as oil and the R isomer eluted second to give 8.0 g of a white solid. The R isomer 1k could be further purified by recrystallization from acetonitrile.

Step l: {(1R,2S,4R)-4-(Acetyl-methyl-amino)-2-[3S-(4-fluorobenzyl)-piperidin-1-ylmethyl]-cyclohexyl}-carbamic acid benzyl ester

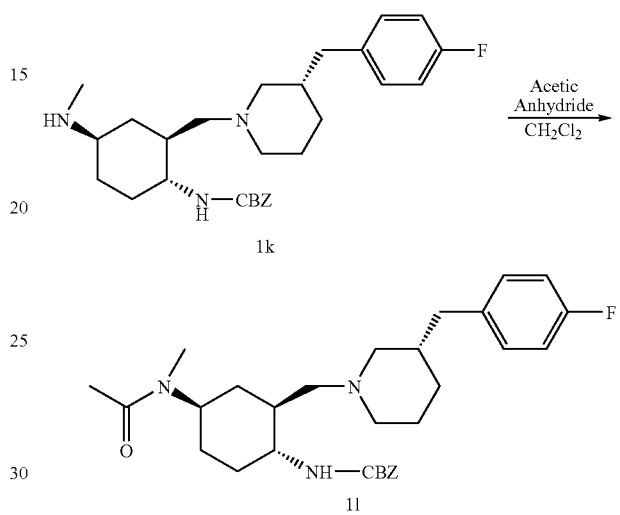

A solution of amine 1k (41.8 g, 89 mmol) in $CH_2Cl_2$ (350 ml) was cooled in an ice bath and treated drop-wise with acetic anhydride (10.0 g, 98 mmol). The solution is stirred for 30 minutes and then washed successively with saturated sodium bicarbonate, 0.5 N NaOH, and brine. The solution was dried over sodium sulfate, filtered and the solvent removed on a rotary evaporator to give 46 g of the amide 1l as a white foam which was used without further purification. NMR shows amide as a mixture of cis and trans isomers (3:1).

¹H NMR (300 MHz, CDCl₃) δ(TMS): 7.90 (bs, 1H), 7.37-7.27 (m, 5H), 6.91-6.80 (m, 4H), 5.08 (m, 2H), 4.56 (m, 0.75H), 3.60 (m, 0.25H), 3.03 (m, 1H), 2.90-2.70 (m, 1H), 2.81 (s, 2.25H), 2.77 (s, 0.75H), 2.60-2.25 (m, 7H), 2.09 (s, 0.75H), 2.08 (m, 1H), 2.07 (s, 2.25H), 1.95-0.81 (m, 11H).

Step m: N-{(3R,4R)-4-Amino-3-[3S-(4-fluorobenzyl)-piperidin-1-ylmethyl]-cyclohexyl}-N-methylacetamide

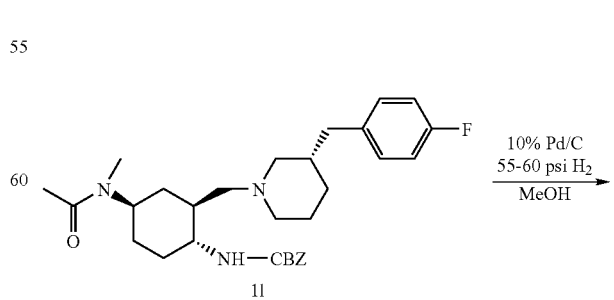

-continued

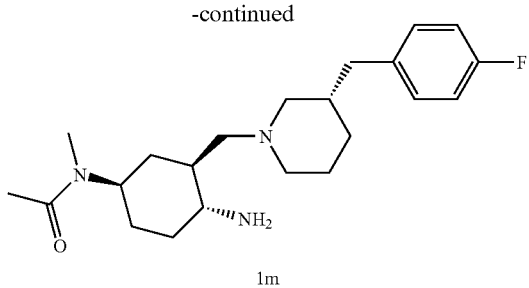

1m

A solution of crude carbamate 11 (45.3 g, 89 mmol) in methanol (100 ml) was treated with 10% Pd/C (10 g) and hydrogenated at 60 psi of hydrogen for 20 hours at room temperature. The catalyst was filtered and the solvent evaporated on a rotary evaporator to give 34 g of amine 1m as a white foam that was used without further purification.

Step n: N-{(3S,4R)-3-[3S-(4-Fluorobenzyl)-piperidin-1-ylmethyl]-4-[3-(4-methyl-thiazol-2-yl)-ureido]-(R)-cyclohexyl}-N-methyl-acetamide

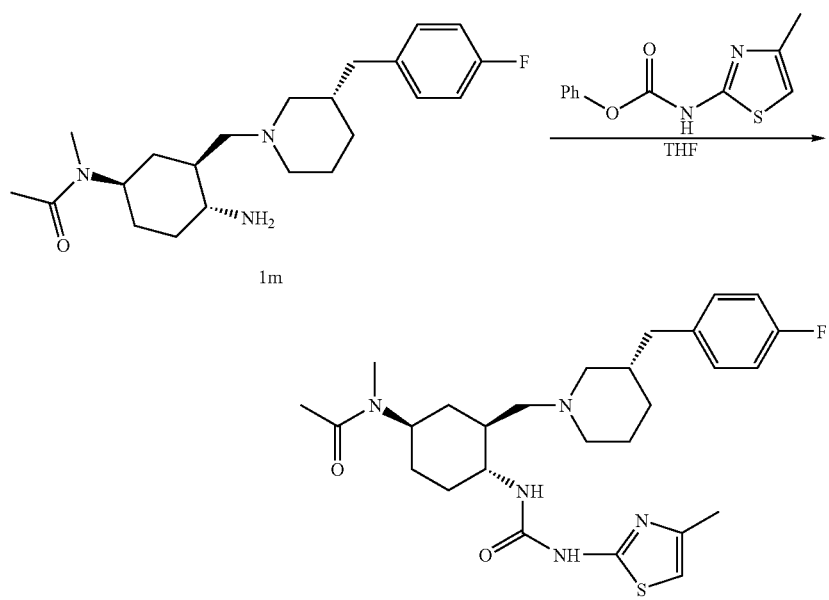

A solution of crude amine 1m (33.4 g, 89 mmol) in THF (400 ml) was treated with (4-Methyl-thiazol-2-yl)-carbamic acid phenyl ester (21.9 g, 93 mmol) and stirred at room temperature overnight. The solvent was removed on a rotary evaporator and the resulting solid dissolved in $CH_2Cl_2$ and chromatographed on 2 Kg of silica gel eluting first with 0.2:1.8:98 $NH_4OH$/MeOH/$CH_2Cl_2$ to remove unreacted carbamate and phenol. Then eluted with 0.8:7.2:92 $NH_4OH$/MeOH/$CH_2Cl_2$ to give 38 g of desired urea. The urea was further purified by recrystallization from 400 ml of acetonitrile to give 34.2 g of crystalline solid. NMR shows mixture of cis/trans amide isomers in 3:1 ratio.

mp 191° C. $[\alpha]^{25}_D$=+9.7° (c=0.640 methanol)

$^1$H NMR (300 MHz, $CDCl_3$) δ(TMS): 8.10 (bs, 0.25H), 7.83 (bs, 0.75H), 7.04-6.99 (m, 2H), 6.80-6.72 (m, 2H), 6.41 (m, 1H), 4.55 (m, 0.75H), 3.60 (m, 0.25H), 3.26 (m, 1H), 2.80-2.77 (m, 1H), 2.82 (s, 2.25H), 2.77 (s, 0.75H), 2.60-2.25 (m, 8H), 2.20-2.00 (m, 1H), 2.11 (s, 3H), 1.95-0.74 (m, 13H).

MS ESI (M+H)$^+$=516.5. Anal. Calcd. for ($C_{27}H_{38}FN_5O_2S$): C, 62.89; H, 7.43; N, 13.58. Found: C, 62.79; H, 7.45; N, 13.43.

The required phenylcarbamates were synthesized using the methods described below.

Method 1: Synthesis of phenyl 4-methylthiazol-2-ylcarbamate

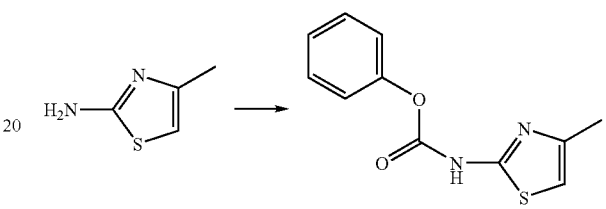

A solution of 2-amino-4-methylthiazole (11.42 g, 0.10 mol) in $CH_2Cl_2$ was cooled to 0° C. in an ice bath and treated with $Et_3N$ (12.1 g, 0.12 mol). While stirring, the mixture was treated with phenyl chloroformate (15.6 g, 0.10 mol) dropwise from an addition funnel. After the addition was complete the mixture was stirred for 10 minutes. The reaction mixture was washed with saturated NaHCO3, water, brine and then dried over $MgSO_4$. The solution was filtered and the solvent removed under vacuum in a rotary evaporator and the resulting solid was chromatographed on silica gel (eluting with 40% ethyl acetate/hexane) to give 12 g of the desired carbamate as a white solid. $^1$H NMR (300 MHz, $CDCl_3$) δ δ 12.38

(bs, 1H), 7.47-7.40 (m, 2H), 7.30-7.19 (m, 3H), 6.52 (d, J=1.1 Hz, 1H), 2.41 (d, J=0.8 Hz, 3H).

Method 2: Synthesis of phenyl 5-acetyl-4-methylthiazol-2-ylcarbamate

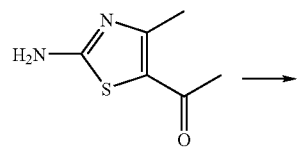

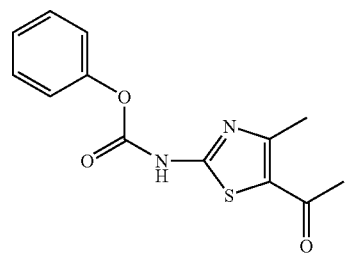

In a round-bottom flask, NaH 60% dispersion in mineral oil (3.07 g, 77 mmol) was washed 2× with hexane and suspended in DMF. Then 2-amino-5-acetyl-4-methyl-thiazole (10.0 g, 64 mmol) was added and stirred while cooling in an ice bath. Stirring continued until the NaH was consumed. Diphenyl carbonate (34 g, 160 mmol) was added while cooling and after the addition was complete the reaction mixture was stirred for an additional 30 minutes at room temperature. The DMF was removed on a rotary evaporator (high vacuum, 40° C.) to yield a brown residue. This residue was dissolved in 1 L of CHCl$_3$ and washed successively with 2 L of 0.5N HCl, 2×1 L of water, and finally by 1 L of brine. The aqueous portions were back extracted twice with 300 ml of CHCl$_3$. The combined organic fractions were dried over anhydrous sodium sulfate, filtered and concentrated on a rotary evaporator to give a white solid. This was chromatographed on silica (15%-70% EtOAc/hexane) to give 15 g of the desired carbamate as a white solid. Mp 180-182° C. $^1$H NMR (300 MHz, CDCl$_3$) δ 11.42 (bs, 1H), 7.47-7.40 (m, 2H), 7.33-7.27 (m, 1H), 7.22-7.18 (m, 2H), 2.72 (s, 3H), 2.50 (s, 3H). ESI MS: (M+H)$^+$=277.1. Anal. Calcd for C$_{13}$H$_{12}$N$_2$O$_3$S: C, 56.51; H, 4.39; N, 10.14; S, 11.60. Found: C, 56.42; H, 4.31; N, 10.11; S, 11.74.

A similar procedure as described above for Example 1 was used to synthesize all the other examples listed in Table 1.

TABLE 1

| Ex. | R$^1$ | R$^2$ | Stereo | ESI MS: (M + H)$^+$ |
|---|---|---|---|---|
| 1 | 4-Methyl-thiazol-2-yl | N-Acetyl-methyl-amino | R | 516.5 |
| 2 | 5-Acetyl-4-methyl-thiazol-2-yl | N-Acetyl-methyl-amino | R | 558.4 |
| 3 | 5-(N,N-Dimethyl-carboxamido)-4-methyl-thiazol-2-yl | N-Acetyl-methyl-amino | R | 587.5 |
| 4 | 2-Methyl-2H-tetrazol-5-yl | N-Acetyl-methyl-amino | R | 501.5 |
| 5 | 2-Methyl-pyridin-4-yl | N-Acetyl-methyl-amino | R | 510.4 |
| 6 | Benzothiazol-2-yl | N-Acetyl-methyl-amino | R | 552 |
| 7 | 5-Methyl-thiazol-2-yl | N-Acetyl-methyl-amino | R | 516.4 |
| 8 | 4-Fluorophenyl | N-Acetyl-methyl-amino | R | 513.4 |
| 9 | 3-Cyanophenyl | N-Acetyl-methyl-amino | R | 520.4 |
| 10 | 1-Methyl-1H-pyrazol-3-yl | N-Acetyl-methyl-amino | R | 499.4 |
| 11 | Thiazol-2-yl | N-Acetyl-methyl-amino | R | 502.3 |
| 12 | 5-tert-Butyl-isoxazol-3-yl | N-Acetyl-methyl-amino | R | 542.6 |
| 13 | 5-tert-Butyl-[1,3,4]thiadiazol-2-yl | N-Acetyl-methyl-amino | R | 559.4 |
| 14 | 5-Methyl-[1,3,4]thiadiazol-2-yl | N-Acetyl-methyl-amino | R | 517.4 |
| 15 | 5-Ethylsulfanyl-[1,3,4]thiadiazol-2-yl | N-Acetyl-methyl-amino | R | 563.4 |
| 16 | 4,5-Dimethyl-thiazol-2-yl | N-Acetyl-methyl-amino | R | 530.4 |
| 17 | 1-(tert-Butoxycarbonyl)-1H-indazol-5-yl | N-Acetyl-methyl-amino | R | 635.7 |
| 18 | 2,3-Dihydro-1-(tert-butoxycarbonyl)-1H-indol-5-yl | N-Acetyl-methyl-amino | R | 636.8 |
| 19 | 1H-Indazol-5-yl | N-Acetyl-methyl-amino | R | 535.6 |
| 20 | 2,3-Dihydro-1H-indol-5-yl | N-Acetyl-methyl-amino | R | 536.6 |
| 21 | 3,4-Dimethyl-isoxazol-5-yl | N-Acetyl-methyl-amino | R | 514.5 |
| 22 | 3,5-Dimethyl-isoxazol-4-yl | N-Acetyl-methyl-amino | R | 514.5 |
| 23 | 5-Trifluoromethyl-[1,3,4]thiadiazol-2-yl | N-Acetyl-methyl-amino | R | 571.3 |
| 24 | 5-Cyclopropyl-[1,3,4]thiadiazol-2-yl | N-Acetyl-methyl-amino | R | 543.6 |
| 25 | 4-tert-Butyl-thiazol-2-yl | N-Acetyl-methyl-amino | R | 558.4 |

TABLE 1-continued

| Ex. | R¹ | R² | Stereo | ESI MS: (M + H)⁺ |
|---|---|---|---|---|
| 26 | [1,3,4]Thiadiazol-2-yl | N-Acetyl-methyl-amino | R | 503.3 |
| 27 | 5-Methyl-isoxazol-3-yl | N-Acetyl-methyl-amino | R | 500.3 |
| 28 | 4-Methyl-benzothiazol-2-yl | N-Acetyl-methyl-amino | R | 566.3 |
| 29 | 6-Methoxy-benzothiazol-2-yl | N-Acetyl-methyl-amino | R | 582.3 |
| 30 | 4-Methoxy-benzothiazol-2-yl | N-Acetyl-methyl-amino | R | 582.3 |
| 31 | 2,6-Dimethyl-pyridin-4-yl | N-Acetyl-methyl-amino | R | 524 |
| 32 | 3-(5-Methyl-tetrazol-1-yl)-phenyl | N-Acetyl-methyl-amino | R | 577.6 |
| 33 | 3-Ethyl-5-(1-methyl-1H-tetrazol-5-yl)-phenyl | N-Acetyl-methyl-amino | R | 605.7 |
| 34 | 3-Cyano-5-(1-methyl-1H-tetrazol-5-yl)-phenyl | N-Acetyl-methyl-amino | R | 602.7 |
| 35 | 3,5-Dimethoxy-phenyl | N-Acetyl-methyl-amino | R | 555.6 |
| 36 | 3,4-Dimethoxy phenyl | N-Acetyl-methyl-amino | R | 554.6 |
| 37 | 3,4,5-Trimethoxy-phenyl | N-Acetyl-methyl-amino | R | 585.6 |
| 38 | 4-tert-Butyl-5-cyano-thiazol-2-yl | N-Acetyl-methyl-amino | R | 583.6 |
| 39 | 3-(Thiazol-2-yl)-phenyl | N-Acetyl-methyl-amino | R | 578.5 |
| 40 | 3-(4,5-Dichloro-1-methyl-1H-imidazol-2-yl)-phenyl | N-Acetyl-methyl-amino | R | 643.6 |
| 41 | 3-Pyrimidin-2-yl-phenyl | N-Acetyl-methyl-amino | R | 573.6 |
| 42 | Benzo[1,3]dioxol-5-yl | N-Acetyl-methyl-amino | R | 539.6 |
| 43 | 7-Methoxy-benzo[1,3]dioxol-5-yl | N-Acetyl-methyl-amino | R | 569.6 |
| 44 | Phenyl | N-Acetyl-methyl-amino | R | 495.4 |
| 45 | 3-Acetyl-Phenyl | N-Acetyl-methyl-amino | R | 537.5 |
| 46 | 3-(1-Methyl-1H-tetrazol-5-yl)-Phenyl | N-Acetyl-methyl-amino | R | 577.5 |
| 47 | Phenyl | N-Acetyl-methyl-amino | S | 495.4 |
| 48 | 3-Acetyl-Phenyl | N-Acetyl-methyl-amino | S | 537.5 |
| 49 | 5-Acetyl-4-methyl-thiazol-2-yl | N-Acetyl-methyl-amino | S | 558.5 |
| 50 | 3-(1-Methyl-1H-tetrazol-5-yl)-Phenyl | N-Acetyl-methyl-amino | S | 577.5 |
| 51 | 5-(N,N-Dimethyl-carboxamide-4-methyl-thiazol)-2-yl | N-Acetyl-methyl-amino | S | 587.5 |
| 52 | 4-Fluorophenyl | N-Acetyl-methyl-amino | S | 513.4 |
| 53 | 3-Cyanophenyl | N-Acetyl-methyl-amino | S | 520.4 |
| 54 | 2-Methyl-2H-tetrazol-5-yl | N-Methanesulfonyl-methyl-amino | R | 537.5 |
| 55 | 5-Acetyl-4-methyl-thiazol-2-yl | N-Methanesulfonyl-methyl-amino | R | 594.4 |
| 56 | 4-Methyl-thiazol-2-yl | N-Methanesulfonyl-methyl-amino | R | 552.4 |
| 57 | Thiazol-2-yl | N-Methanesulfonyl-methyl-amino | R | 538.4 |
| 58 | 1-Methyl-1H-pyrazol-3-yl | N-Methanesulfonyl-methyl-amino | R | 535.4 |
| 59 | [1,3,4]Thiadiazol-2-yl | N-Methanesulfonyl-methyl-amino | R | 539.4 |
| 60 | 3-Acetyl-Phenyl | N-Methanesulfonyl-methyl-amino | R | 573.4 |
| 61 | Phenyl | N-Methanesulfonyl-methyl-amino | R | 531.4 |
| 62 | 4-Fluorophenyl | N-Methanesulfonyl-methyl-amino | R | 549.3 |
| 63 | 3-Cyanophenyl | N-Methanesulfonyl-methyl-amino | R | 556.3 |
| 64 | 5-Methyl-[1,3,4]thiadiazol-2-yl | N-Methanesulfonyl-methyl-amino | R | 553.4 |
| 65 | 4,5-Dimethyl-thiazol-2yl | N-Methanesulfonyl-methyl-amino | R | 566.4 |
| 66 | 5-tert-Butyl-isoxazol-3-yl | N-Methanesulfonyl-methyl-amino | R | 578.5 |
| 67 | 5-tert-Butyl-[1,3,4]thiadiazol-2-yl | N-Methanesulfonyl-methyl-amino | R | 595.5 |
| 68 | 5-Ethylsulfanyl-[1,3,4]thiadiazol-2-yl | N-Methanesulfonyl-methyl-amino | R | 599.4 |
| 69 | 5-Trifluoromethyl-[1,3,4]thiadiazol-2-yl | N-Methanesulfonyl-methyl-amino | R | 607.4 |
| 70 | 5-Cyclopropyl-[1,3,4]thiadiazol-2-yl | N-Methanesulfonyl-methyl-amino | R | 579.4 |

TABLE 1-continued

| Ex. | R¹ | R² | Stereo | ESI MS: (M + H)⁺ |
|---|---|---|---|---|
| 71 | 4-tert-Butyl-thiazol-2-yl | N-Methanesulfonyl-methyl-amino | R | 594.4 |
| 72 | 5-Methyl-thiazol-2-yl | N-tert-butoxy-carbonyl-methyl-amino | R | 574.4 |
| 73 | 1-Methyl-1H-pyrazol-3-yl | N-tert-butoxy-carbonyl-methyl-amino | R | 557.5 |
| 74 | 2,3-Dihydro-1-(tert-butoxy-carbonyl)-1H-indol-5-yl | N-tert-butoxy-carbonyl-methyl-amino | R | 694.6 |
| 75 | 4-methyl-thiazol-2-yl | N-tert-Butoxy-carbonyl-methyl-amino | R | 574.5 |
| 76 | 2-Methyl-2H-tetrazol-5-yl | Acetyl-amino | R | 487.4 |
| 77 | 5-Methyl-thiazol-2-yl | Acetyl-amino | R | 502.4 |
| 78 | 4-Methyl-thiazol-2-yl | Acetyl-amino | R | 502.2 |
| 79 | Thiazol-2-yl | Acetyl-amino | R | 488.2 |
| 80 | [1,3,4]Thiadiazol-2-yl | Acetyl-amino | R | 489.2 |
| 81 | 1-Methyl-1H-pyrazol-3-yl | Acetyl-amino | R | 485.2 |
| 82 | 5-methyl-isoxazol-3-yl | Acetyl-amino | R | 486.2 |
| 83 | 5-Acetyl-4-methyl-thiazol-2-yl | Acetyl-amino | R | 544.3 |
| 84 | 5-tert-Butyl-isoxazol-3-yl | Acetyl-amino | R | 528.5 |
| 85 | 5-tert-Butyl-[1,3,4]thiadiazol-2-yl | Acetyl-amino | R | 545.5 |
| 86 | 5-Methyl-[1,3,4]thiadiazol-2-yl | Acetyl-amino | R | 503.4 |
| 87 | 5-Ethylsulfanyl-[1,3,4]thiadiazol-2-yl | Acetyl-amino | R | 549.4 |
| 88 | 4,5-Dimethyl-thiazol-2yl | Acetyl-amino | R | 516.4 |
| 89 | 2,6-Dimethyl-pyridin-4-yl | Acetyl-amino | R | 510 |
| 90 | 1-(tert-Butoxycarbonyl)-1H-indazol-5-yl | Acetyl-amino | R | 621.7 |
| 91 | 2,3-Dihydro-1-(tert-butoxycarbonyl)-1H-indol-5-yl | Acetyl-amino | R | 622.7 |
| 92 | 1H-Indazol-5-yl | Acetyl-amino | R | 521.5 |
| 93 | 2,3-Dihydro-1H-indol-5-yl | Acetyl-amino | R | 522.5 |
| 94 | 4-Methyl-thiazol-2-yl | Acetyl-amino | R | 502.4 |
| 95 | 2-Methyl-pyridin-4-yl | Acetyl-amino | R | 496.4 |
| 96 | 3,4-Dimethyl-isoxazol-5-yl | Acetyl-amino | R | 500.4 |
| 97 | 3,5-Dimethyl-isoxazol-4-yl | Acetyl-amino | R | 500.4 |
| 98 | 5-Trifluoromethyl-[1,3,4]thiadiazol-2-yl | Acetyl-amino | R | 557.5 |
| 99 | 5-cyclopropyl-[1,3,4]thiadiazol-2-yl | Acetyl-amino | R | 529.5 |
| 100 | 4-tert-Butyl-thiazol-2-yl | Acetyl-amino | R | 544.4 |
| 101 | 2-Methyl-2H-tetrazol-5-yl | N-Acetyl-cyclopropyl-amino | R | 527.5 |
| 102 | 5-Acetyl-4-methyl-thiazol-2-yl | N-Acetyl-cyclopropyl-amino | R | 584.4 |
| 103 | 4-Methyl-thiazol-2-yl | N-Acetyl-cyclopropyl-amino | R | 542.4 |
| 104 | 5-Methyl-thiazol-2-yl | N-Acetyl-cyclopropyl-amino | R | 542.4 |
| 105 | 1-Methyl-1H-pyrazol-3-yl | N-Acetyl-cyclopropyl-amino | R | 525.5 |
| 106 | 5-tert-Butyl-[1,3,4]thiadiazol-2-yl | N-Acetyl-cyclopropyl-amino | R | 585.4 |
| 107 | 5-tert-Butyl-isoxazol-3-yl | N-Acetyl-cyclopropyl-amino | R | 568.4 |
| 108 | 4-Methyl-thiazol-2-yl | N-Acetyl-isopropyl-amino | R | 544.3 |
| 109 | 4-Methyl-thiazol-2-yl | 2-Oxo-piperidin-1-yl | R | 542.3 |
| 110 | 5-Methyl-thiazol-2-yl | 2-Oxo-piperidin-1-yl | R | 542.3 |
| 111 | 5-Acetyl-4-methyl-thiazol-2-yl | 2-Oxo-piperidin-1-yl | R | 584.3 |
| 112 | [1,3,4]Thiadiazol-2-yl | 2-Oxo-piperidin-1-yl | R | 529.3 |
| 113 | Thiazol-2-yl | 2-Oxo-piperidin-1-yl | R | 528.3 |
| 114 | 4-Methyl-thiazol-2-yl | N-Acetyl-propyl-amino | R | 544.3 |
| 115 | 4-Methyl-thiazol-2-yl | N-Acetyl-ethyl-amino | R | 530.4 |
| 116 | 2-Methyl-2H-tetrazol-5-yl | N-Methanesulfonyl-cyclopropyl-amino | R | 563.4 |
| 117 | 5-Acetyl-4-methyl-thiazol-2-yl | N-Methanesulfonyl-cyclopropyl-amino | R | 620.5 |

TABLE 1-continued

| Ex. | R¹ | R² | Stereo | ESI MS: (M + H)⁺ |
|---|---|---|---|---|
| 118 | 4-Methyl-thiazol-2-yl | N-Methanesulfonyl-cyclopropyl-amino | R | 578.4 |
| 119 | 5-Methyl-thiazol-2-yl | N-Methanesulfonyl-cyclopropyl-amino | R | 578.3 |
| 120 | 1-Methyl-1H-pyrazol-3-yl | N-Methanesulfonyl-cyclopropyl-amino | R | 561.4 |
| 121 | 5-tert-Butyl-[1,3,4]thiadiazol-2-yl | N-Methanesulfonyl-cyclopropyl-amino | R | 621.5 |
| 122 | 5-tert-Butyl-isoxazol-3-yl | N-Methanesulfonyl-cyclopropyl-amino | R | 604.5 |
| 123 | 5-Acetyl-4-methyl-thiazol-2-yl | Methyl-amino | R | 516.4 |
| 124 | 4-Methyl-thiazol-2-yl | Methyl-amino | R | 474.3 |
| 125 | 2,3-Dihydro-1H-indol-5-yl | Methyl-amino | R | 494.3 |
| 126 | 5-Acetyl-4-methyl-thiazol-2-yl | Cyclopropyl-amino | R | 542.5 |
| 127 | 5-Methyl-isoxazol-3-yl | Cyclopropyl-amino | R | 484.4 |
| 128 | 1-Methyl-1H-pyrazol-3-yl | Cyclopropyl-amino | R | 483.4 |
| 129 | 4-Methyl-thiazol-2-yl | Ethyl-amino | R | 488.3 |
| 130 | 4-Fluoro-phenyl | Dimethyl-amino | R | 485.5 |
| 131 | Benzothiazol-2-yl | Dimethyl-amino | R | 524 |
| 132 | 5-Methyl-thiazol-2-yl | Morpholin-4-yl | R | 530.5 |
| 133 | Phenyl | Dimethyl-amino | R | 467.5 |
| 134 | 3-Acetyl-Phenyl | Dimethyl-amino | R | 509.5 |
| 135 | 5-Acetyl-4-methyl-thiazol-2-yl | Dimethyl-amino | R | 530.5 |
| 136 | 3-(1-Methyl-1H-tetrazol-5-yl)-phenyl | Dimethyl-amino | R | 549.5 |
| 137 | 3-Acetyl-Phenyl | Morpholin-4-yl | R | 551.3 |
| 138 | 5-Acetyl-4-methyl-thiazol-2-yl | Morpholin-4-yl | R | 572.3 |
| 139 | 3-(1-Methyl-1H-tetrazol-5-yl)-phenyl | Morpholin-4-yl | R | 591.3 |
| 140 | 4-Methyl-thiazol-2-yl | Morpholin-4-yl | R | 530.3 |
| 141 | 3,5-Diacetyl-Phenyl | Morpholin-4-yl | R | 593.4 |
| 142 | 3,5-Diacetyl-Phenyl | Dimethyl-amino | R | 551.3 |
| 143 | 4-Methyl-thiazol-2-yl | Dimethyl-amino | R | 488.3 |
| 144 | Thiazol-2-yl | Dimethyl-amino | R | 474.2 |
| 145 | [1,3,4]Thiadiazol-2-yl | Dimethyl-amino | R | 475.1 |
| 146 | 1-Methyl-1H-pyrazol-3-yl | Dimethyl-amino | R | 471.2 |
| 147 | 5-Methyl-isoxazol-3-yl | Dimethyl-amino | R | 472.2 |
| 148 | 2,3-Dihydro-1H-indol-5-yl | Dimethyl-amino | R | 508.3 |
| 149 | 1H-Indazol-5-yl | Dimethyl-amino | R | 507.3 |
| 150 | 3-Acetyl-5-cyano-Phenyl | Dimethyl-amino | R | 534.3 |
| 151 | 3-Acetyl-5-fluoro-Phenyl | Dimethyl-amino | R | 527 |
| 152 | 3-Bromo-5-cyano-phenyl | Dimethyl-amino | R | 570; 572 |
| 153 | 3-(5-Methyl-1H-tetrazol-1-yl)-Phenyl | Dimethyl-amino | R | 549 |
| 154 | Pyridin-4-yl | Dimethyl-amino | R | 468 |
| 155 | 2-Methyl-pyridin-4-yl | Dimethyl-amino | R | 482 |
| 156 | Phenyl | N-Methyl-propyl amino | R | 495.3 |
| 157 | 3-(1-Hydroxy-ethyl)-Phenyl | Dimethyl-amino | R | 511.5 |
| 158 | 5-(1R-Hydroxy-ethyl)-4-methyl-Thiazol-2-yl | Dimethyl-amino | R | 532.4 |
| 159 | 5-(1S-Hydroxy-ethyl)-4-methyl-thiazol-2-yl | Dimethyl-amino | R | 532.4 |
| 160 | Methyl | Dimethyl-amino | R | 405 |
| 161 | 4-tert-Butyl-5-cyano-thiazol-2-yl | Dimethyl-amino | R | 555 |
| 162 | Adamantan-1-yl | Dimethyl-amino | R | 525 |
| 163 | 3,4-Dicyano-phenyl | Dimethyl-amino | R | 517 |
| 164 | 3,5-Di-isoxazol-3-yl-phenyl | Dimethyl-amino | R | 601 |
| 165 | 2-Methyl-2H-tetrazol-5-yl | Dimethyl-amino | R | 473.4 |
| 166 | 2-Methyl-2H-tetrazol-5-yl | Morpholin-4-yl | R | 515.6 |
| 167 | 5-tert-Butyl-isoxazol-3-yl | Morpholin-4-yl | R | 556.6 |
| 168 | 5-tert-Butyl-[1,3,4]thiadiazol-2-yl | Morpholin-4-yl | R | 573.5 |
| 169 | 5-tert-Butyl-isoxazol-3-yl | Dimethyl-amino | R | 514.6 |
| 170 | 5-tert-Butyl-[1,3,4]thiadiazol-2-yl | Dimethyl-amino | R | 531.5 |
| 171 | 4-Methyl-thiazol-2-yl | 4-Methyl-3-oxo-piperazin-1-yl | R | 557.3 |

TABLE 1-continued

| Ex. | R¹ | R² | Stereo | ESI MS: (M + H)⁺ |
|---|---|---|---|---|
| 172 | 4-Methyl-thiazol-2-yl | Pyrrolidin-1-yl | R | 514.3 |
| 173 | 4-Methyl-thiazol-2-yl | 3-Oxo-piperazin-1-yl | R | 543.4 |
| 174 | 4-Methyl-thiazol-2-yl | Diethyl-amino | R | 516.4 |
| 175 | 4-Methyl-thiazol-2-yl | Azetidin-1-yl | R | 500.3 |
| 176 | 5-Acetyl-4-methyl-thiazol-2-yl | Piperidin-1-yl | R | 570.3 |
| 177 | 4-Methyl-thiazol-2-yl | Piperidin-1-yl | R | 528.4 |
| 178 | 5-Methyl-thiazol-2-yl | Piperidin-1-yl | R | 528.4 |
| 179 | 5-tert-Butyl-isoxazol-3-yl | Piperidin-1-yl | R | 554.4 |
| 180 | Thiazol-2-yl | Piperidin-1-yl | R | 514.4 |
| 181 | 4-tert-Butyl-thiazol-2-yl | Piperidin-1-yl | R | 570.3 |
| 182 | 4-Methyl-5-(pyrrolidin-1-ylmethyl)-thiazol-2-yl | Pyrrolidin-1-yl | R | 597.3 |
| 183 | 4-tert-Butyl-thiazol-2-yl | Morpholin-4-yl | R | 572.3 |
| 184 | 4,5-Dimethyl-thiazol-2yl | Morpholin-4-yl | R | 544.3 |
| 185 | Thiazol-2yl | Morpholin-4-yl | R | 516.3 |
| 186 | 5-Cyclopropyl-[1,3,4]thiadiazol-2-yl | Morpholin-4-yl | R | 557.3 |
| 187 | 5-Trifluoromethyl-[1,3,4]thiadiazol-2-yl | Morpholin-4-yl | R | 585.2 |
| 188 | 5-Methyl-[1,3,4]thiadiazol-2-yl | Morpholin-4-yl | R | 531.3 |
| 189 | [1,3,4]Thiadiazol-2-yl | Morpholin-4-yl | R | 517.3 |
| 190 | 1-Methyl-1H-pyrazol-3-yl | Morpholin-4-yl | R | 513.4 |
| 191 | 4-Methoxy-benzothiazol-2-yl | Morpholin-4-yl | R | 596.4 |
| 192 | 6-Methoxy-benzothiazol-2-yl | Morpholin-4-yl | R | 596.4 |
| 193 | 4-Methyl-benzothiazol-2-yl | Morpholin-4-yl | R | 580.4 |
| 194 | 4-Fluorophenyl | Dimethyl-amino | S | 485.3 |
| 195 | Phenyl | Morpholin-4-yl | S | 509.3 |
| 196 | Phenyl | Dimethyl-amino | S | 467.5 |
| 197 | 3-Acetyl-phenyl | Dimethyl-amino | S | 509.5 |
| 198 | 5-Acetyl-4-methyl-thiazol-2-yl | Dimethyl-amino | S | 530.5 |
| 199 | 3-(1-Methyl-1H-tetrazol-5-yl)-phenyl | Dimethyl-amino | S | 549.6 |
| 200 | Phenyl | Ethyl-amino | S | 481.3 |
| 201 | Phenyl | Methyl-propyl-amino | S | 495.3 |
| 202 | 5-Acetyl-4-methyl-thiazol-2-yl | Methanesulfonyl-amino | R | 580.4 |
| 203 | 1-Methyl-1H-pyrazol-3-yl | Methanesulfonyl-amino | R | 521.5 |
| 204 | Thiazol-2-yl | Methanesulfonyl-amino | R | 524.5 |
| 205 | 4-Methyl-thiazol-2-yl | Methanesulfonyl-amino | R | 538.4 |
| 206 | 5-Methyl-thiazol-2-yl | Methanesulfonyl-amino | R | 538.4 |
| 207 | [1,3,4]Thiadiazol-2-yl | Methanesulfonyl-amino | R | 525.4 |
| 208 | 5-tert-Butyl-[1,3,4]thiadiazol-2-yl | Methanesulfonyl-amino | R | 581.4 |
| 209 | 5-tert-Butyl-isoxazol-3-yl | Methanesulfonyl-amino | R | 564.4 |
| 210 | 3-(1-Methyl-1H-tetrazol-5-yl)-phenyl | N-Methyl-cyclopropyl-amino | R | 575.3 |
| 211 | 3-Ethyl-5-(1-methyl-1H-tetrazol-5-yl)-phenyl | N-Methyl-cyclopropyl-amino | R | 603.3 |
| 212 | 5-Acetyl-4-methyl--thiazol-2-yl | N-Methyl-cyclopropyl-amino | R | 556.3 |
| 213 | 4-Methyl-thiazol-2-yl | N-Methyl-cyclopropyl-amino | R | 514.2 |
| 214 | 5-Ethyl-[1,3,4]thiadiazol-2-yl | Morpholin-4-yl | R | 545.2 |
| 215 | 5-Ethyl-[1,3,4]thiadiazol-2-yl | N-Acetyl-methyl-amino | R | 531.2 |
| 216 | 5-Ethyl-[1,3,4]thiadiazol-2-yl | Acetyl-amino | R | 517.1 |
| 217 | 5-Ethyl-[1,3,4]thiadiazol-2-yl | N-tert-butoxy-carbonyl-amino | R | 575.2 |
| 218 | 1-Methyl-1H-pyrazol-2-yl | Morpholin-4-yl | R | 527.3 |
| 219 | 1-Methyl-1H-pyrazol-2-yl | N-Acetyl-methyl-amino | R | 513.2 |
| 220 | 1-Methyl-1H-pyrazol-2-yl | Acetyl-amino | R | 499.2 |
| 221 | [1,3,4]Thiadiazol-2-yl | Isobutyryl-amino | R | 517.2 |
| 222 | 5-Methyl-[1,3,4]thiadiazol-2-yl | Isobutyryl-amino | R | 531.2 |
| 223 | 5-Ethyl-[1,3,4]thiadiazol-2-yl | Isobutyryl-amino | R | 545.2 |
| 224 | 4,5-Dimethyl-thiazol-2yl | Isobutyryl-amino | R | 544.2 |
| 225 | 4-Methyl-thiazol-2-yl | Isobutyryl-amino | R | 530.2 |

TABLE 1-continued

| Ex. | R¹ | R² | Stereo | ESI MS: (M + H)⁺ |
|---|---|---|---|---|
| 226 | 5-Methyl-thiazol-2-yl | Isobutyryl-amino | R | 530.2 |
| 227 | Isopropyl | N-Acetyl-methyl-amino | R | 461.2 |
| 228 | Cyclopentanyl | N-Acetyl-methyl-amino | R | 487.2 |
| 229 | Cyclohexanyl | N-Acetyl-methyl-amino | R | 501.2 |
| 230 | 5-Isopropyl-[1,3,4]thiadiazol-2-yl | N-Acetyl-methyl-amino | R | 545.1 |
| 231 | 5-Isopropyl-[1,3,4]thiadiazol-2-yl | Acetyl-amino | R | 531.1 |
| 232 | 5-Isopropyl-[1,3,4]thiadiazol-2-yl | Isobutyryl-amino | R | 559.2 |
| 233 | Methyl | Morpholin-4-yl | R | 447.2 |
| 234 | Isopropyl | Morpholin-4-yl | R | 475.3 |
| 235 | Cyclopentanyl | Morpholin-4-yl | R | 501.34 |
| 236 | Cyclohexanyl | Morpholin-4-yl | R | 515.36 |
| 237 | 5-Isobutyl-[1,3,4]thiadiazol-2-yl | Morpholin-4-yl | R | 559.2 |
| 238 | [1,3,4]Thiadiazol-2-yl | N-2,2,3,3,3-pentafluoro-propionyl-amino | R | 593.2 |
| 239 | 5-Methyl-[1,3,4]thiadiazol-2-yl | N-2,2,3,3,3-pentafluoro-propionyl-amino | R | 607.2 |
| 240 | 5-Ethyl-[1,3,4]thiadiazol-2-yl | N-2,2,3,3,3-pentafluoro-propionyl-amino | R | 621.2 |
| 241 | 5-Isopropyl-[1,3,4]thiadiazol-2-yl | N-2,2,3,3,3-pentafluoro-propionyl-amino | R | 635.3 |
| 242 | 5-Cyclopropyl-[1,3,4]thiadiazol-2-yl | N-2,2,3,3,3-pentafluoro-propionyl-amino | R | 633.3 |
| 243 | 5-Trifluoromethyl-[1,3,4]thiadiazol-2-yl | N-2,2,3,3,3-pentafluoro-propionyl-amino | R | 661.2 |
| 244 | Thiazol-2-yl | N-2,2,3,3,3-pentafluoro-propionyl-amino | R | 592.2 |
| 245 | 5-Methyl-thiazol-2-yl | N-2,2,3,3,3-pentafluoro-propionyl-amino | R | 606.2 |
| 246 | 4-Methyl-thiazol-2-yl | N-2,2,3,3,3-pentafluoro-propionyl-amino | R | 606.3 |
| 247 | 4,5-Dimethyl-thiazol-2-yl | N-2,2,3,3,3-pentafluoro-propionyl-amino | R | 620.3 |
| 248 | [1,3,4]Thiadiazol-2-yl | Propionyl-amino | R | 503.4 |
| 249 | 5-Methyl-[1,3,4]thiadiazol-2-yl | Propionyl-amino | R | 517.4 |
| 250 | 5-Ethyl-[1,3,4]thiadiazol-2-yl | Propionyl-amino | R | 531.4 |
| 251 | 5-Isopropyl-[1,3,4]thiadiazol-2-yl | Propionyl-amino | R | 545.4 |
| 252 | 5-Cyclopropyl-[1,3,4]thiadiazol-2-yl | Propionyl-amino | R | 543.4 |
| 253 | 5-Trifluoromethyl-[1,3,4]thiadiazol-2-yl | Propionyl-amino | R | 571.4 |
| 254 | Thiazol-2-yl | Propionyl-amino | R | 502.4 |
| 255 | 5-Methyl-thiazol-2-yl | Propionyl-amino | R | 516.4 |
| 256 | 4-Methyl-thiazol-2-yl | Propionyl-amino | R | 516.4 |
| 257 | 4,5,-Dimethyl-thiazol-2-yl | Propionyl-amino | R | 530.4 |
| 258 | 5-Methyl-thiazol-2-yl | N-Acetyl-tert-butyl-amino | R | 558.3 |
| 259 | 4-Methyl-thiazol-2-yl | N-Acetyl-tert-butyl-amino | R | 558.3 |
| 260 | 5-methyl-isoxazol-3-yl | N-Acetyl-tert-butyl-amino | R | 542.4 |
| 261 | [1,3,4]Thiadiazol-2-yl | N-Acetyl-tert-butyl-amino | R | 545.3 |
| 262 | 2-Methyl-2H-tetrazol-5-yl | N-Acetyl-tert-butyl-amino | R | 543.4 |
| 263 | 5-Methyl-[1,3,4]thiadiazol-2-yl | N-Acetyl-tert-butyl-amino | R | 559.3 |
| 264 | 1-Methyl-1H-pyrazol-3-yl | N-Acetyl-tert-butyl-amino | R | 541.4 |
| 265 | Thiazol-2-yl | N-Acetyl-tert-butyl-amino | R | 544.3 |
| 266 | Thiazol-5-yl | Acetyl-amino | R | 488.6 |
| 267 | Pyrimidin-2-yl | Acetyl-amino | R | 483.6 |
| 268 | Pyrimidin-2-yl | N-Acetyl-methyl-amino | R | 497.2 |
| 269 | Thiazol-5-yl | N-Acetyl-methyl-amino | R | 502.7 |
| 270 | Pyrimidin-2-yl | Morpholin-4-yl | R | 511.2 |
| 271 | Thiazol-5-yl | Morpholin-4-yl | R | 516.1 |
| 272 | 6-Methoxy-pyrimidin-4-yl | Acetyl-amino | R | 513.7 |
| 273 | 6-Methoxy-pyrimidin-4-yl | N-Acetyl-methyl-amino | R | 527.5 |
| 274 | 6-Methoxy-pyrimidin-4-yl | Morpholin-4-yl | R | 541.2 |
| 275 | 3-Methyl-isoxazol-5-yl | Acetyl-amino | R | 486.4 |
| 276 | 3-Methyl-isoxazol-5-yl | N-Acetyl-methyl-amino | R | 500.4 |
| 277 | 3-Methyl-isoxazol-5-yl | Morpholin-4-yl | R | 514.3 |
| 278 | 4-Oxo-4,5-dihydro-thiazol-2-yl | Acetyl-amino | R | 504.2 |
| 279 | 4-Methyl-oxazol-2-yl | N-Acetyl-methyl-amino | R | 500.3 |

TABLE 1-continued

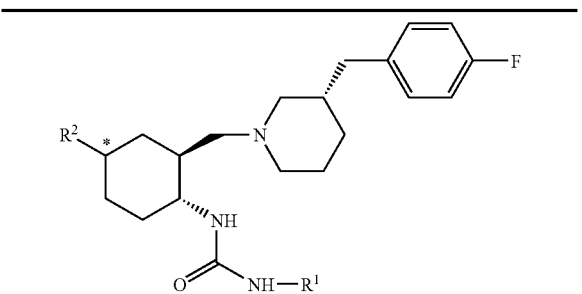

| Ex. | R[1] | R[2] | Stereo | ESI MS: (M + H)+ |
|---|---|---|---|---|
| 280 | 3-Cyano-4-fluoro-phenyl | Acetyl-amino | R | 524.2 |
| 281 | 3-Cyano-4-fluoro-phenyl | N-Acetyl-methyl-amino | R | 538.2 |
| 282 | 3-Cyano-4-fluoro-phenyl | Morpholin-4-yl | R | 552.2 |
| 283 | 3,4-Dicyano-phenyl | Acetyl-amino | R | 531.3 |
| 284 | 3,4-Dicyano-phenyl | N-Acetyl-methyl-amino | R | 545.3 |
| 285 | 3,4-Dicyano-phenyl | Morpholin-4-yl | R | 559.3 |
| 286 | Pyridin-2-yl | Acetyl-amino | R | 482.2 |
| 287 | Pyridin-2-yl | N-Acetyl-methyl-amino | R | 496.3 |
| 288 | Pyridin-2-yl | Morpholin-4-yl | R | 510.3 |
| 289 | Pentafluorophenyl | Acetyl-amino | R | 571.1 |
| 290 | Pentafluorophenyl | N-Acetyl-methyl-amino | R | 585.13 |
| 291 | Pentafluorophenyl | Morpholin-4-yl | R | 599.1 |
| 291.1 | [1,3,4]Thiadiazol-2-yl | N-3,3-dimethylbutanoyl-Amino | R | 545.48 |
| 291.2 | 5-trifluoromethyl-[1,3,4]thiadiazol-2-yl | N-3,3-dimethylbutanoyl-Amino | R | 613.42 |
| 291.3 | 5-Ethyl-[1,3,4]thiadiazol-2-yl | N-3,3-dimethylbutanoyl-Amino | R | 573.48 |
| 291.4 | 5-Isopropyl-[1,3,4]thiadiazol-2-yl | N-3,3-dimethylbutanoyl-Amino | R | 587.5 |
| 291.5 | [1,3,4]thiadiazol-2-yl | N-3-methylbutanoyl-Amino | R | 531.47 |

TABLE 1-continued

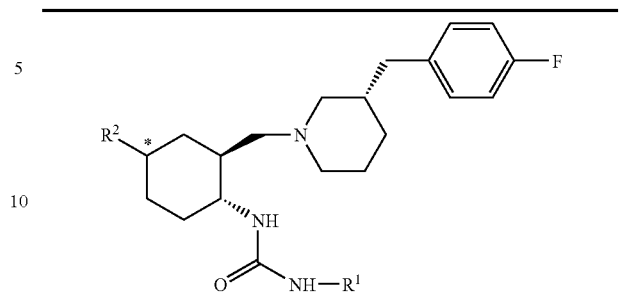

| Ex. | R[1] | R[2] | Stereo | ESI MS: (M + H)+ |
|---|---|---|---|---|
| 291.6 | 5-trifluoromethyl-[1,3,4]thiadiazol-2-yl | N-3-methylbutanoyl-Amino | R | 599.51 |
| 291.7 | 5-Ethyl-[1,3,4]thiadiazol-2-yl | N-3-methylbutanoyl-Amino | R | 559.45 |
| 291.8 | 5-Isopropyl-[1,3,4]thiadiazol-2-yl | N-3-methylbutanoyl-Amino | R | 573.48 |

Compounds of formula I can also be synthesized as outlined in Schemes 6-7. For 5-substituted cyclohexyl compounds, 3-ethoxy-2-cyclohexen-1-one 20 is acylated with 2 equivalents of diethyl carbonate and 2 equivalents of lithium bis(trimethylsilyl)amide to give the keto-ester 21. The enol ether is hydrolized with 70% aqueous acetic acid to give the diketo-ester 22, which is converted to the ketal-keto-ester 23 with 1.05 equivalent of ethylene glycol and catalytic amount of p-toluenesulfonic acid in benzene. The intermediate 23 is then treated with R-(+)-α-methylbenzylamine in the presence of acetic acid in benzene to give the enamine 24. The enamine is reduced with sodium triacetoxyborohydride in the presence of ethylene glycol and acetic acid in methylene chloride to give the (1R,2S)-cis-amino-ester 25. The ester is then isomerized with sodium tert-butoxide in THF to give the (1R,2R)-trans-amino-ester 26, which is reduced to the corresponding alcohol 27 with lithium aluminum hydride. Removal of the chiral auxiliary under a catalytic hydrogenolysis condition with palladium hydroxide gives the (1R, 2R)-amino-alcohol 28.

SCHEME 6

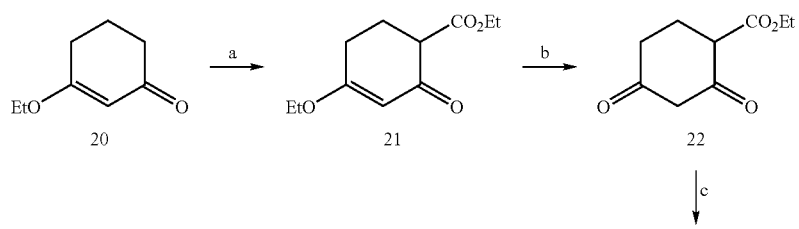

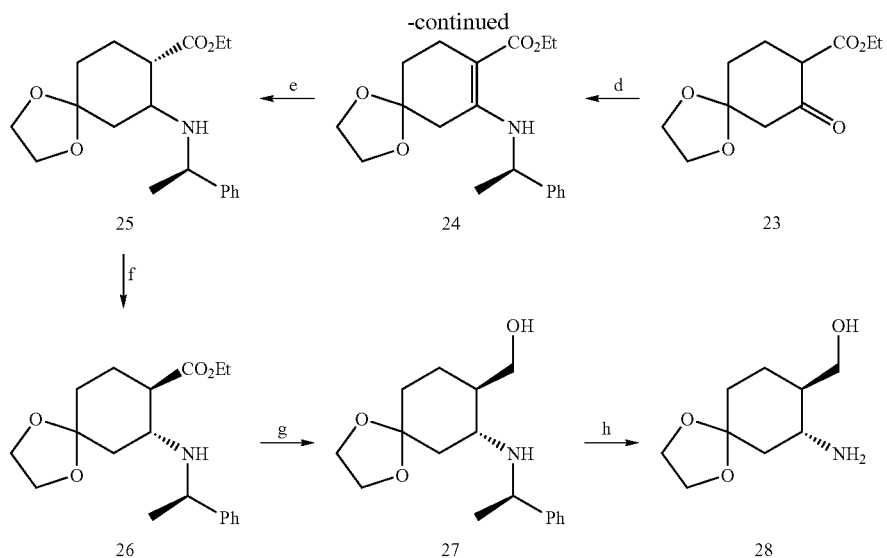

a. 2 eq. LiHMDS, 2 eq. (EtO)₂CO, THF.
b. 70% aq. HOAc, 60° C.
c. ethylene glycol, p-TsOH, benzene.
d. (R)-(+)-α-methylbenzylamine, HOAc, benzene.
e. Na(OAc)₃BH, HOAc, ethylene glycol, CH₂Cl₂.
f. NaOtBu, THF.
g. LiAlH₄, ether.
h. H₂, Pd(OH)₂, methanol.

Introduction of the substitution group $R^2$ is shown in Scheme 7. (1R,2R)-amino-alcohol 28 is selectively protected on the nitrogen with benzyl chloroformate in the presence of aqueous sodium carbonate to give the CBz-protected amino-alcohol 29. A Swern oxidation of the alcohol gives the corresponding aldehyde 30. It is then coupled with (3S)-3-(4-fluorobenzyl)piperidine by a reductive amination with sodium triacetoxyborohydride or sodium cyanoborohydride to afford the 2-[3-(4-fluorobenzyl)piperidinyl]methyl-cyclohexylamine derivative 31. The ketal of the intermediate 31 is hydrolyzed with 1N HCl in acetonitrile to give the ketone 32. A reductive amination of the ketone 32 with methyl amine or methyl amine hydrochloride and sodium cyanoborohydride or sodium triacetoxyborohydride in methylene chloride, dichloroethane or methanol gives the methyl amine derivative 31 ($R^a$=CH₃, $R^b$=H). The methylamino group can be converted to an amide or an sulfonamide using a suitable acylating or sulfonylating agent. Other $R^2$ groups can be introduced either directly through the ketone 32 or through the corresponding alcohol, which can be obtained by a reduction of the ketone 32.

The CBz-protecting group of the amine of the intermediate 31 is removed by a catalytic hydrogenation to give the free amine 32, which is reacted with an isocyanate, a thioisocyanate or a phenyl carbamate to give the urea 33, a compound of formula I. Example 210 was prepared according to this scheme.

SCHEME 7

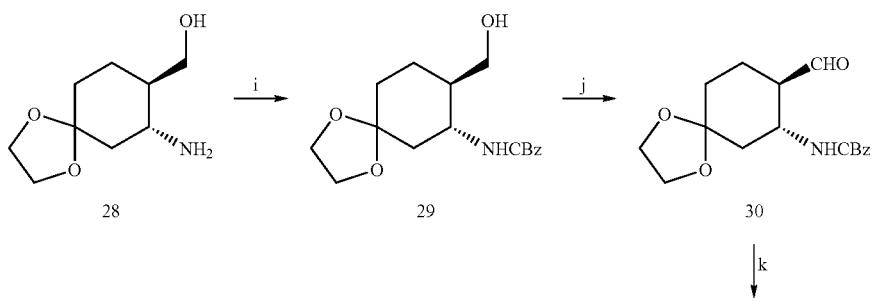

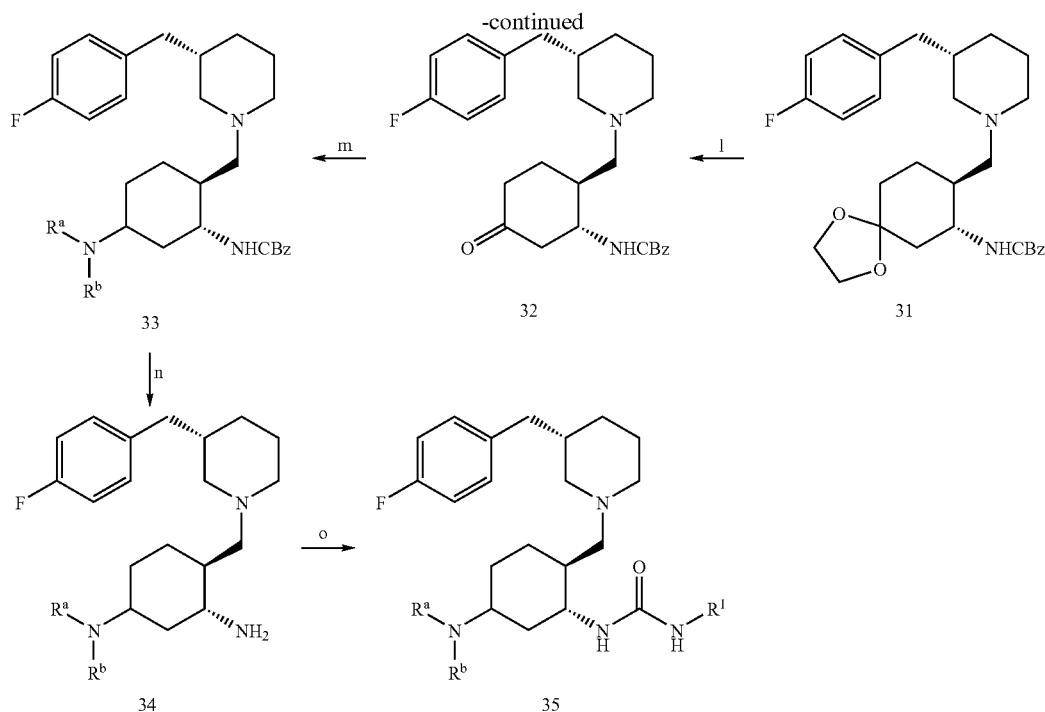

i. Benzyl chloroformate, aq. Na$_2$CO$_3$, CH$_2$Cl$_2$.
j. DMSO, (COCl)$_2$, NEt$_3$, CH$_2$Cl$_2$.
k. R$^4$R$^5$NH, Na(OAc)$_3$BH, CH$_2$Cl$_2$.
l. 1N HCl, CH$_3$CN.
m. R$^a$R$^b$NH, Na(OAc)$_3$BH, CH$_2$Cl$_2$.
n. H$_2$, 10% Pd/C, MeOH,
o. R$^1$NCO or R$^1$NHCOOPh, THF.

Example 292

N-(1R,2S,5R)-{4-[3-(4-Fluoro-benzyl)-piperidin-1-ylmethyl]-3-[3-(4-methyl-thiazol-2-yl)-ureido]-cyclohexyl}-N-methyl-acetamide

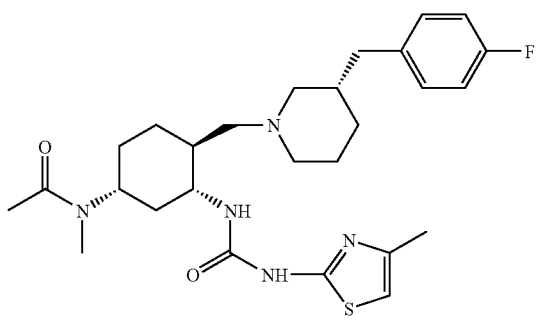

Step a: 4-Ethoxy-2-oxo-cyclohex-3-ene-carboxylic acid ethyl ester

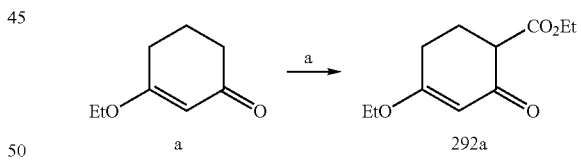

To a stirred solution of a (50 g) and diethyl carbonate (86.6 ml, 2 equiv.) in 750 mL of anhydrous THF at −78° C. was added 720 mL of LiHMDS in THF (2 equiv.) dropwise over a period of 1.5 hrs, and then the temperature was raised to room temperature gradually. It was stirred for 2 days at room temperature and poured into a mixture of 1N HCl (1 L) and ice (~700 g) with stirring. The product was extracted with EtOAc (3×) and the combined extracts were washed with brine, sat'd NaHCO$_3$ and brine. It was dried over Na$_2$SO$_4$ and evaporated to give a solid residue. It was crystallized from EtOAc and hexane to give pure keto-ester 292a (65 g, 87% yield).

$^1$H NMR (300 MHz, CDCl$_3$) δ 5.39 (s, 1H), 4.22 (q, 2H, J=7.0 Hz), 3.92 (q, 2H, J=7.0 Hz), 3.32 (dd, 1H, J$_1$=8.8 Hz, J$_2$=5.1 Hz), 2.62-2.12 (m, 4H), 1.37 (t, 3H, J=7.0 Hz), 1.29 (t, 3H, J=7.0 Hz).

Step b. 2,4-Dioxo-cyclohexanecarboxylic acid ethyl ester

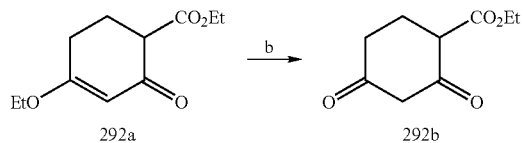

A solution of keto-ester 292a (60.3 g) in 694 mL of 70% aq. acetic acid was stirred for 6 hrs at 60° C. and cooled to room temperature. The acid and water were evaporated off under reduced pressure and the syrupy residue was dried by azeotroping with benzene three times to give crude diketone-ester 292b.

Step c: 7-oxo-1,4-dioxa-spiro[4.5]decane-8-carboxylic acid ethyl ester

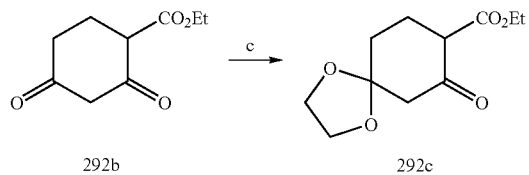

To a solution of diketone-ester 292b in 710 mL of benzene were added ethylene glycol (16.6 mL, 1.05 equiv.) and p-toluenesulfonic acid monohydrate (0.69 g, 0.013 equiv.), and it was refluxed under a Dean-Stock trap for 2 hrs. After cooling to room temperature it was made basic with sat'd NaHCO$_3$, and the product was extracted with EtOAc (3×). The combined extracts were washed with brine, dried over Na$_2$SO$_4$, and evaporated to give a syrupy residue. It was purified by column chromatography (silica gel, 15% EtOAc/hexane) to give ketal-keto-ester 292c (35 g, 54% yield for 2 steps) as a light yellow oil.

$^1$H NMR (300 MHz, CDCl$_3$) δ 12.21 (s, 1H), 4.22 (q, 2H, J=7.0 Hz), 4.00 (s, 4H), 2.53 (s, 2H), 2.41 (t, 2H, J=6.6 Hz), 1.77 (t, 2H, J=6.6 Hz, 1.30 (t, 3H, J=7.0 Hz).

Step d: 7-(1-Phenyl-ethylamino)-1,4-dioxa-spiro[4.5]dec-7-ene-8-carboxylic acid ethyl ester

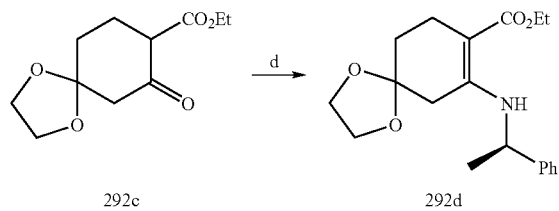

To a solution of ketal-keto-ester 292c (54 g) in 1 L of benzene were added (R)-(+)-α-methylbenzylamine (31.7 mL, 1.04 equiv.) and acetic acid (27 mL, 2 equiv.), and it was refluxed under a Dean-Stock trap for 2 hrs. After cooling to room temperature it was added to 1 L of sat'd NaHCO$_3$ with stirring, and the organic layer was separated. It was washed with brine, dried over Na$_2$SO$_4$, and evaporated to give a syrupy residue of crude enamine 292d. It was dried further by azeotroping with benzene three times, and used without purification for next step.

Step e: (1R,2S)-7-(1-Phenyl-ethylamino)-1,4-dioxa-spiro[4.5]decane-8-carboxylic acid ethyl ester

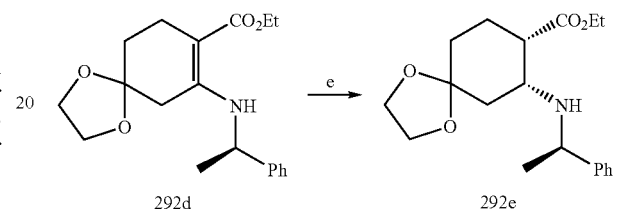

To a solution of enamine 292d in 1 L of anhydrous CH$_2$Cl$_2$ were added ethylene glycol (69.4 mL, 5 equiv.) and acetic acid (158 mL, 11.1 equiv.) at 0° C., and was also added Na(OAc)$_3$BH (211 g, 4 equiv.) in five equal portions over a period of 2 hrs. The mixture was stirred for 14 hrs at room temperature, and then was made basic with sat'd Na$_2$CO$_3$. The organic layer was separated and the aqueous solution was extracted with CH$_2$Cl$_2$ (2×200 mL). The combined extracts were washed with water, dried over MgSO$_4$, and evaporated to give an oily residue. The residue was dissolved in a 1:1 mixture of EtOAc and hexane (800 mL), and washed with water (4×150 mL) and with brine (2×100 mL) to remove ethylene glycol and excess methylbenzylamine. The solution was dried over Na$_2$SO$_4$ and evaporated to give a syrupy residue of crude cis amino-ester 292e as a ~3:1 mixture of (1R, 2S)- and (1S,2R)-diastereomers. It was dried further by azeotroping with benzene three times, and used without purification for next step.

Step f: ((1R,2R)-7-(1-Phenyl-ethylamino)-1,4-dioxa-spiro[4.5]decane-8-carboxylic acid ethyl ester

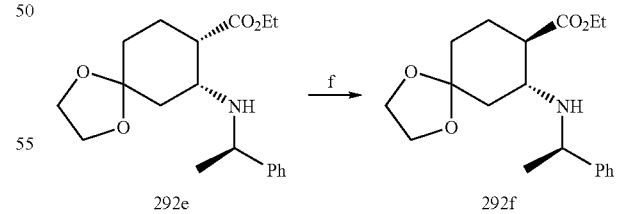

Step f: To a solution of cis amino-ester 292e in 900 mL of anhydrous THF was added sodium t-butoxide (23.8 g, 1 equiv.), and the mixture was stirred for 5.5 hrs at room temperature. It was then poured into a vigorously stirred mixture of 1N HCl (350 mL) and ice (ca. 500 g). After stirring for 5 minutes it was made basic with 250 mL of sat'd NaHCO$_3$, and extracted with 500 mL of EtOAc. The extract was washed with sat'd NaHCO$_3$ and brine. The combined aqueous layers were extracted with 300 mL of EtOAc again and washed with brine. The EtOAc extracts were combined, dried over $Na_2SO_4$, and evaporated to give a ~3:1 mixture of trans amino-ester 292f [as a 3:1 mixture of (1R,2R)- and (1S,2S)-diastereomers] and cis amino-ester 292e [as a 3:1 mixture of (1S,2R)- and (1R,2S)-diastereomers]. (1S,2S)-Diastereomer of the trans amino-ester ($R_f$=0.17, 40% EtOAc/hexane) was separated out from other diastereomers ($R_f$>0.3, 40% EtOAc/hexane) by column chromatography (silica gel, 15-40% EtOAc/hexane). Fractions containing the (1R,2R)-trans amino-ester 292f ($R_f$=0.33, 40% EtOAc/hexane) were combined and evaporated to give a syrupy residue (39.4 g).

$^1$H NMR (300 MHz, $CDCl_3$) δ 7.30-7.20 (m, 5H), 4.18 (q, 2H, J=7.3 Hz), 3.87-3.78 (m, 5H), 3.07 (dt, 1H, $J_1$=9.8 Hz, $J_2$=3.3 Hz), 2.20 (dt, 1H, J=9.38 Hz, $J_2$=3.3 Hz), 1.92-1.42 (m, 6H), 1.29 (t, 3H, J=6.6 Hz), 1.28 (d, 3H, J=6.6 Hz).

Step g: ((1R,2R)-[7-(1-Phenyl-ethylamino)-1,4-dioxa-spiro[4.5]dec-8-yl]-methanol

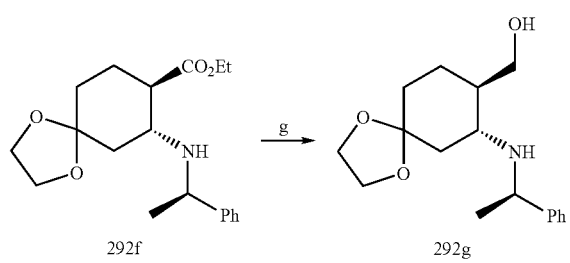

To a solution of crude (1R,2R)-trans amino-ester 292f (39.4 g) in 600 mL of anhydrous diethyl ether at 0° C. was added dropwise a 1M solution of $LiAlH_4$ in THF (132 mL, 1.1 equiv.), and the mixture was stirred for 1.5 hrs at the same temperature. The reaction was quenched by slow addition of $Na_2SO_4.10H_2O$ (~50 g), and stirring for 45 minutes. It was filtered through a plug of Celite and evaporated to give a crystalline solid. It was recrystallized from EtOAc and hexane to afford (1R,2R)-trans amino-alcohol 292 g (28.7 g, 39.7% yield for 4 steps).

$^1$H NMR (300 MHz, $CDCl_3$) δ 7.35-7.23 (m, 5H), 3.92-3.88 (m, 4H), 3.71-3.65 (m, 2H), 2.82 (td, 1H, $J_1$=11.7 Hz, $J_2$=4.0 Hz), 2.08 (dt, 1H, $J_1$=12.7 Hz, $J_2$=2.5 Hz), 1.73-1.12 (m, 7H), 1.41 (d, 3H, J=6.6 Hz).

Step h: ((1R,2R)-(7-Amino-1,4-dioxa-spiro[4.5]dec-8-yl)-methanol

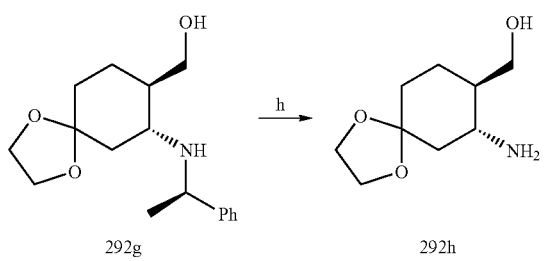

To a solution of (1R,2R)-trans amino-alcohol 292 g (10 g, 34.3 mmoles) in 100 mL of methanol was added 1 g of $Pd(OH)_2$ under nitrogen. The mixture was treated with $H_2$ on a parr hydrogenator (60 psi) for 48 hrs. The catalyst was filtered off and the filtrate was evaporated to give aminoalcohol 292h as an oil, Which was used for next reaction without purification.

Step i: (1R,2R)-{8-Hydroxymethyl-1,4-dioxa-spiro[4.5]dec-7-yl}-carbamic acid benzyl ester

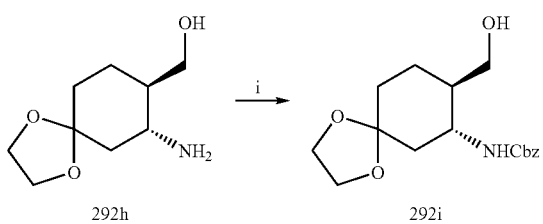

To a solution of (1R,2R)-trans aminoalcohol 292h (34.3 mmoles) in 200 mL of $CH_2Cl_2$ and 125 mL of sat'd $NaHCO_3$ at 0° C. was added benzyl chloroformate (6.1 mL, 1.25 equiv.) dropwise and the mixture was stirred for 0.5 hrs. Then the $CH_2Cl_2$ layer was separated and the aqueous layer was extracted with $CH_2Cl_2$. The combined extracts were washed with water, dried over $MgSO_4$, and evaporated to give a solid residue. It was crystallized from EtOAc and Hexane to give pure Cbz-protected amino-alcohol 292i (9.7 g, yield 88% for 2 steps).

$^1$H NMR (300 MHz, $CDCl_3$) δ 7.35 (s, 5H), 5.1 (s, 2H), 4.92 (d, 1H, J=8.4 Hz), 3.94 (s, 4H), 3.80-3.69 (m, 2H), 3.47 (t, 1H, J=10.9 Hz), 3.15 (m, 1H), 2.06-1.20 (m, 6H).

Step j: {(7R,8R)-(8-Formyl-1,4-dioxa-spiro[4.5]dec-7-yl)-carbamic acid benzyl ester

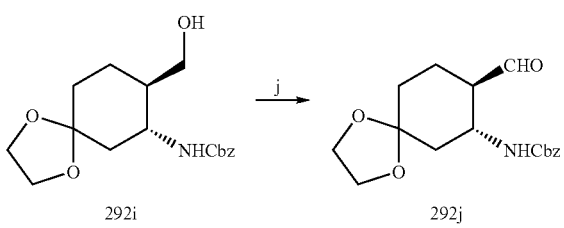

To a stirred solution of oxalyl chloride (5.51 mL, 1.5 equiv.) in 190 mL of anhydrous $CH_2Cl_2$ at −65° C. was added DMSO (4.8 mL, 1.6 equiv.) dropwise over a period of 10 minutes. The mixture was stirred for 20 minutes at −65~−60° C. Then a solution of pure CBz-protected amino-alcohol 292i (13.54 g) in 95 mL of anhydrous $CH_2Cl_2$ was added dropwise over a period of 20 minutes at −70~−60° C. After stirring for 40 minutes at −60~−50° C. triethylamine (17.6 mL, 3 equiv.) was added dropwise over a period of 10 minutes, and the mixture was continued to stir for 1.25 hrs at −50~0° C. Then 500 mL of diethyl ether was added. The organic layer was washed with water (2×150 mL) and brine (100 mL). It was dried over $Na_2SO_4$ and evaporated to give a solid residue. Recrystallization from EtOAc and hexane provided aldehyde 292j (13.2 g, 98% yield).

$^1$H NMR (300 MHz, $CDCl_3$) δ 9.67 (s, 1H), 7.35 (m, 5H), 5.62 (bs, 1H), 5.10 (m, 2H), 4.37 (m, 1H), 3.98 (m, 4H), 2.50 (m, 1H), 1.92 (m, 2H), 1.61 (m, 4H).

Step k: {(7R,8S)-{8-[3-(4-Fluoro-benzyl)-piperidin-1-ylmethyl]-1,4-dioxa-spiro[4.5]dec-7-yl}-carbamic acid benzyl ester

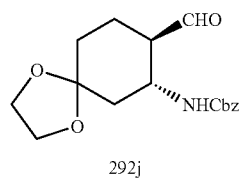
292j

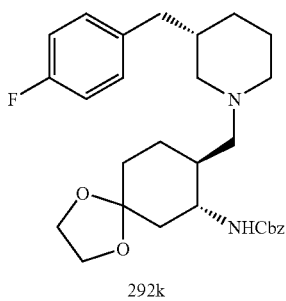
292k

To a solution of 3S-(4-fluorobenzyl)piperidine mandelate salt (15.1 g, 1.2 equiv.) in 200 mL of CH$_2$Cl$_2$ was added 1 N NaOH (87.4 ml), and the mixture was stirred for 15 min at room temperature. The CH$_2$Cl$_2$ was evaporated. The water layer was extracted with CH$_2$Cl$_2$ (2×). The combined CH$_2$Cl$_2$ layers were washed with water, brine, dried over MgSO$_4$, and evaporated to give an oil residue. A solution of this free base and crude aldehyde 17 (11.6 g, 0.346 mol) in 325 ml CH$_2$Cl$_2$ was cooled in an ice water and treated with Na(OAc)$_3$BH (15.43 g, 72.78 mmol). The resulting mixture was stirred for 2 hrs at room temperature. It was quenched with sat'd Na$_2$CO$_3$ (220 ml) and the product was extracted with CH$_2$Cl$_2$ (2×). The combined extracts were washed with brine, dried over MgSO$_4$, and evaporated to give an oily residue. It was purified by column chromatography (silica gel, EtOAc) to give pure amino-ketal 292k (15 g, 83% yield).

$^1$H NMR (300 MHz, CDCl$_3$) δ 7.67 (s, br, 1H), 7.33 (m, 5H), 6.91 (m, 4H), 5.08 (s, 2H), 3.93 (bs, 4H), 3.47 (m, 1H), 2.83 (m, 1H), 2.60-1.24 (m, 19H).

Step l. (1R,2S)-{2-[3-(4-Fluoro-benzyl)-piperidin-1-ylmethyl]-5-oxo-cyclohexyl}-carbamic acid benzyl ester

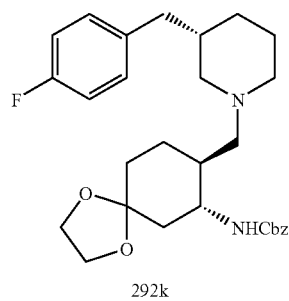
292k

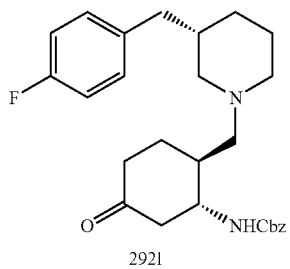
292l

To a solution of amino-ketal 292k (12.0 g) in 145 mL of CH$_3$CN was added 242 mL of 1N HCl (q), and the mixture was stirred for 20 hrs at room temperature. It was then made basic with sat'd Na$_2$CO$_3$ and extracted with EtOAc (2×). The combined extracts were washed with brine, dried over MgSO$_4$, and evaporated to give crude amino-ketone 292l (10.92 g) as an oil, which was used for next step without purification.

$^1$H NMR (300 MHz, CDCl$_3$) δ 7.86 (s, br 1H), 7.35 (m, 5H), 6.91 (m, 4H), 5.09 (s, 2H), 3.48 (m, 1H), 3.14 (m, 1H), 2.89 (m, 1H), 2.60 (m, 1H), 2.48-1.36 (m, 16H), 0.95 (m, 1H).

Step m. (1R,2S,5R)-{5-(Acetyl-methyl-amino)-2-{3-(4-fluoro-benzyl)-piperidin-1-ylmethyl}-cyclohexyl}-carbamic acid benzyl ester

Step m1. (1R,2S,5R)-{2-[(3-(4-Fluoro-benzyl)-piperidin-1-ylmethyl]-5-methylamino-cyclohexyl}-carbamic acid benzyl ester

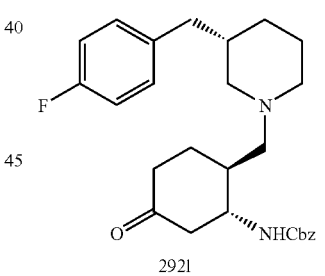
292l

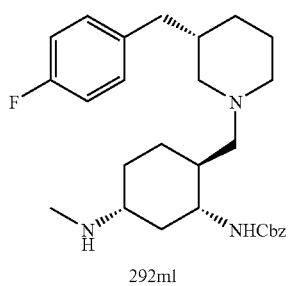
292m1

To a solution of amino-ketone 292l (958 mg) in 10 mL of MeOH was added methylamine HCl salt (1.43 g), and the mixture was stirred for 15 min. Then Na(OAc)$_3$BH (266 mg) was added and the resulting mixture was stirred for 20 hrs at room temperature. The reaction was quenched with sat'd Na$_2$CO$_3$ (10 mL) and extracted with EtOAc (2×). The combined extracts were washed with brine, dried over Na$_2$SO$_4$, and evaporated to give a ~1:1 mixture of (5R)- and (5S)-diastereomers. (1R,2S,5R)-isomer was separated out by column chromatography (silica gel, 0.5:5:95 cNH$_4$OH/CH$_3$OH/CH$_2$Cl$_2$) to give (5R)—N-methylacetamide 292m1 (329.5 mg) as an oil.

(5R)-isomer: $^1$H NMR (300 MHz, CDCl$_3$) δ 7.81 (brs, 1H), 7.36 (m, 5H), 6.90 (m, 4H), 5.10 (m, 2H), 3.15 (m, 2H), 2.81 (m, 2H), 2.42 (s, 3H), 0.89-2.64 (m, 18H).

Step m2. (1R,2S,5R)-{5-(Acetyl-methyl-amino)-2-[3-(4-fluoro-benzyl)-piperidin-1-ylmethyl]-cyclohexyl}-carbamic acid benzyl ester

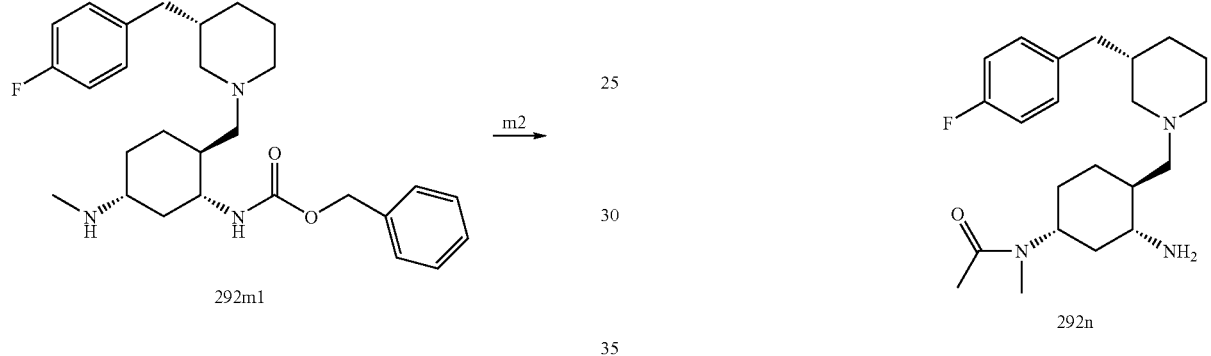

To a solution of 1-methylamine 292 ml (329.5 g) in 7 mL of anhydrous CH$_2$Cl$_2$ were added acetic anhydride (80 μL, 1.2 equiv.) and triethylamine (196.4 μL, 2 equiv.), and the mixture was stirred at room temperature for 2 hrs. The reaction was quenched with MeOH and extracted with EtOAc (2×). The combined extracts were washed with brine, dried over Na$_2$SO$_4$, and evaporated. The crude product was purified by column chromatography to give 5-N-methylacetamide 292m2 (200 mg) as an oil.

$^1$H NMR (300 MHz, CDCl$_3$) δ 8.03 (s, br, 1H) 7.37 (m, 5H), 6.90 (m, 4H), 5.08 (s, 2H), 5.08 (m, 2H), 4.51 (m, 1H), 3.60 (m, 1H), 3.20 (m, 2H), 2.80 (d, 3H), 2.06 (s, 3H), 2.60-1.3 (m, 18H).

Step n. (1R,2S,5R)—N-{3-Amino-4-[3-(4-fluoro-benzyl)-piperidin-1-ylmethyl]-cyclohexyl}-N-methyl-acetamide (21)

To a solution of 5R-5-N-methylacetamide 292m2 (467.8 mg) in 25 mL of methanol was added 10% Pd/C (200 mg) under nitrogen, and the mixture was placed on the Parr under H$_2$ (60 psi) for 18 hrs. The catalyst was filtered off and the filtrate was concentrated to give cyclohexylamine 292n as an clear oil (350 mg).

Step o. (1R,2S,5R)—N-{4-[3-(4-Fluoro-benzyl)-piperidin-1-ylmethyl]-3-[3-(4-methyl-thiazol-2-yl)-ureido]-cyclohexyl}-N-methyl-acetamide

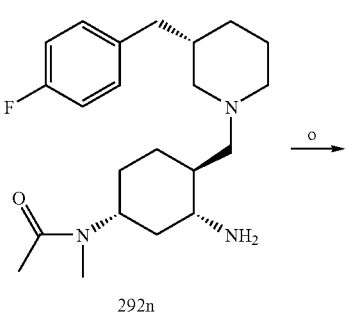

-continued

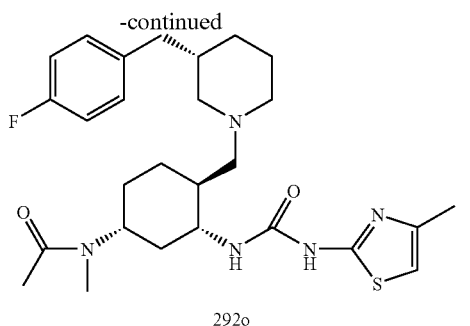

292o

To a solution of disubstituted cyclohexylamine 292n (60 mg) in 2 mL of anhydrous THF was added (4-Methyl-thiazol-2-yl)-carbamic acid phenyl ester (41.2 mg), and the mixture was stirred for overnight at room temperature. After evaporating off the solvent, the crude product were purified by flash chromatography (silica gel, 90% $CH_2Cl_2$/MeOH) to give cyclohexylurea 292o as amorphous solid.

$^1$H NMR (300 MHz, $CD_3OD$) δ 7.05 (m, 2H), 6.89 (m, 2H), 6.52 (d, 1H), 4.42 (m, 1H), 3.78 (m, 1H), 3.48 (m, 2H), 2.88 (s, 1.5H), 2.76 (s, 1.5H), 2.40 (m, 4H), 2.30 (s, 3H), 2.15 (s, 1.5H), 2.08 (s, 1.5H), 2.03-0.91 (m, 14H). MS ESI $(M+H)^+$ =516.4.

A similar procedure as described above for Example 292 was used to synthesize all the other examples listed in Table 2.

TABLE 2

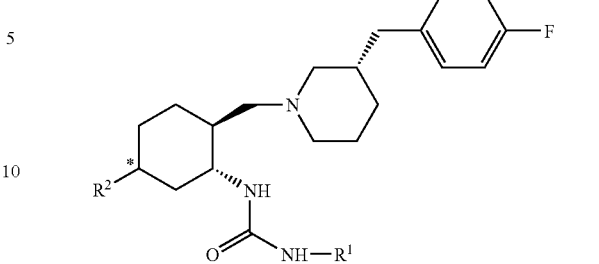

| Ex | $R^2$ | $R^3$ | Stereo | MS (M + H)+ |
|---|---|---|---|---|
| 292 | 4-Methyl-thiazol-2-yl | N-Acetyl-methyl-amino | R | 516.4 |
| 293 | 5-Acetyl-4-methyl-thiazol-2-yl | Dimethyl-amino | R | 530.1 |
| 294 | 3-Acetyl-phenyl | Dimethyl-amino | R | 509.2 |
| 296 | 4-Methyl-thiazol-2-yl | Acetyl-amino | R | 502.1 |
| 297 | 5-Acetyl-4-methyl-thiazol-2-yl | Acetyl-amino | R | 544.2 |
| 298 | 3-(1-Methyl-1H-tetrazol-5-yl)-phenyl | Acetyl-amino | R | 563.2 |
| 299 | 3-Acetyl-phenyl | Acetyl-amino | R | 523.1 |
| 300 | 4-Methyl-thiazol-2-yl | Formyl-amino | R | 488.3 |
| 301 | 5-Acetyl-4-methyl-thiazol-2-yl | N-Acetyl-methyl-amino | R | 558.3 |
| 302 | 3-(1-Methyl-1H-tetrazol-5-yl)-phenyl | N-Acetyl-methyl-amino | R | 577.4 |
| 303 | 3-Acetyl-phenyl | N-Acetyl-methyl-amino | R | 537.4 |
| 304 | 1-Methyl-1H-indazol-5-yl | N-Acetyl-methyl-amino | R | 549.4 |
| 305 | 5-Acetyl-4-methyl-thiazol-2-yl | Formyl-amino | R | 530.3 |
| 306 | 3-(1-Methyl-1H-tetrazol-5-yl)-phenyl | Formyl-amino | R | 549.4 |
| 307 | 3-Acetyl-phenyl | Formyl-amino | R | 509.3 |
| 308 | 1-Methyl-1H-indazol-5-yl | Formyl-amino | R | 521.4 |
| 309 | 1-Methyl-1H-indazol-5-yl | Dimethyl-amino | R | 521.4 |
| 310 | 2-Methyl-pyridin-4-yl | Dimethyl-amino | R | 482.3 |
| 311 | 3-(1-Methyl-1H-tetrazol-5-yl)-phenyl | Dimethyl-amino | R | 549.4 |
| 312 | 3-(1-Methyl-1H-tetrazol-5-yl)-phenyl | Methanesulfonyl-amino | R | 599.3 |
| 313 | 5-Acetyl-4-methyl-thiazol-2-yl | Methanesulfonyl-amino | R | 580.3 |
| 314 | 4-Methyl-thiazol-2-yl | Dimethyl-amino | R | 488.2 |
| 315 | 5-Acetyl-4-methyl-thiazol-2-yl | Dimethyl-amino | S | 530.1 |
| 316 | 3-(1-Methyl-1H-tetrazol-5-yl)-phenyl | Dimethyl-amino | S | 549.2 |
| 317 | 3-Acetyl-phenyl | Dimethyl-amino | S | 509.1 |
| 318 | 5-Acetyl-4-methyl-thiazol-2-yl | Acetyl-amino | S | 544.1 |
| 319 | 4-Methyl-thiazol-2-yl | Formyl-amino | S | 488.3 |
| 320 | 5-Acetyl-4-methyl-thiazol-2-yl | Formyl-amino | S | 530.4 |
| 321 | 3-(1-Methyl-1H-tetrazol-5-yl)-phenyl | Formyl-amino | S | 549.4 |
| 322 | 3-Acetyl-phenyl | Formyl-amino | S | 509.4 |
| 323 | 1-Methyl-1H-indazol-5-yl | Formyl-amino | S | 521.4 |
| 324 | 2,6-Dimethyl-pyridin-4-yl | Formyl-amino | S | 496.4 |
| 325 | 4-Methyl-thiazol-2-yl | N-Acetyl-methyl-amino | S | 516.4 |
| 326 | 5-Acetyl-4-methyl-thiazol-2-yl | N-Acetyl-methyl-amino | S | 558.4 |
| 327 | 3-(1-Methyl-1H-tetrazol-5-yl)-phenyl | N-Acetyl-methyl-amino | S | 577.4 |
| 328 | 3-Acetyl-phenyl | N-Acetyl-methyl-amino | S | 537.5 |
| 329 | 1-Methyl-1H-indazol-5-yl | N-Acetyl-methyl-amino | S | 549.5 |
| 330 | 1-Methyl-1H-indazol-5-yl | Dimethyl-amino | S | 521.5 |
| 331 | 2-Methyl-pyridin-4-yl | Dimethyl-amino | S | 482.4 |
| 332 | 1-Methyl-1H-pyrazol-3-yl | Dimethyl-amino | S | 471.3 |
| 333 | 3-(1-Methyl-1H-tetrazol-5-yl)-phenyl | Morpholin-4-yl | S | 591.3 |
| 334 | 2-Methyl-pyridin-4-yl | Morpholin-4-yl | S | 563.3 |
| 335 | 4-Methyl-5-acetyl-thiazol-2-yl | Morpholin-4-yl | S | 572.2 |
| 336 | 3-(1-Methyl-1H-tetrazol-5-yl)-phenyl | N-Methyl-cyclopropyl-amino | R | 575.2 |
| 337 | 3-Ethyl-5-(1-methyl-1H-tetrazol-5-yl)-phenyl | N-Methyl-cyclopropyl-amino | R | 603.2 |
| 338 | 4-Methyl-5-acetyl-thiazol-2-yl | N-Methyl-cyclopropyl-amino | R | 556.2 |
| 339 | 4-Methyl-thiazol-2-yl | N-Methyl-cyclopropyl-amino | R | 514.2 |

TABLE 2-continued

| Ex | R² | R³ | Stereo | MS (M + H)+ |
|----|----|----|--------|-------------|
| 340 | 4-Methyl-thiazol-2-yl | N-Methyl-cyclopropyl-amino | S | 514.4 |
| 341 | 4-Methyl-5-acetyl-thiazol-2-yl | N-Methyl-cyclopropyl-amino | S | 556.1 |
| 342 | 3-Ethyl-5-(1-methyl-1H-tetrazol-5-yl)-phenyl | N-Methyl-cyclopropyl-amino | S | 603.2 |
| 343 | 3-(1-Methyl-1H-tetrazol-5-yl)-phenyl | N-Methyl-cyclopropyl-amino | S | 575.3 |

An alternative synthesis of select compounds of this invention is shown in Scheme 8. The known protected β-aminoester 36 (Kobayashi, et al., *Tetrahedron Lett.* 1984, 25, 2557; Abell and Gardiner, *Org. Lett.* 2002, 4, 3663; Wipf and Wang, *Tetrahedron Lett.* 2000, 41, 8747) is readily hydrolyzed and then coupled with ammonia to provide amide 37, which may be further transformed to acyl carbamate 38. Cyclization of the lithio anion of 38 with iodine provides 39 (for a related reaction, see: Taguchi, et al., *J. Org. Chem.* 1997, 62, 7330). Compound 39 may be deiodinated and reduced to provide 40, which may be functionalized through reductive amination with a variety of amines. In the instance of the present invention, coupling with 3-(para-fluorobenzyl) piperidine provides compound 41. As described in the schemes and examples above, compound 41 is readily functionalized to provide compounds of the current invention, generalized in structure 42. For example, for the synthesis of Example 83, compound 41 is first treated with TEA to remove the tert-butylcarbamate protecting group, and the resulting amine is acetylated with acetic anhydride to provide the acetamide. Hydrogenolysis of the benzylcarbamate provides a primary amine which may be reacted with 5-acetyl-4-methylthiazol-2-ylcarbamate (synthesis described in the examples above) to provide the compound of Example 83.

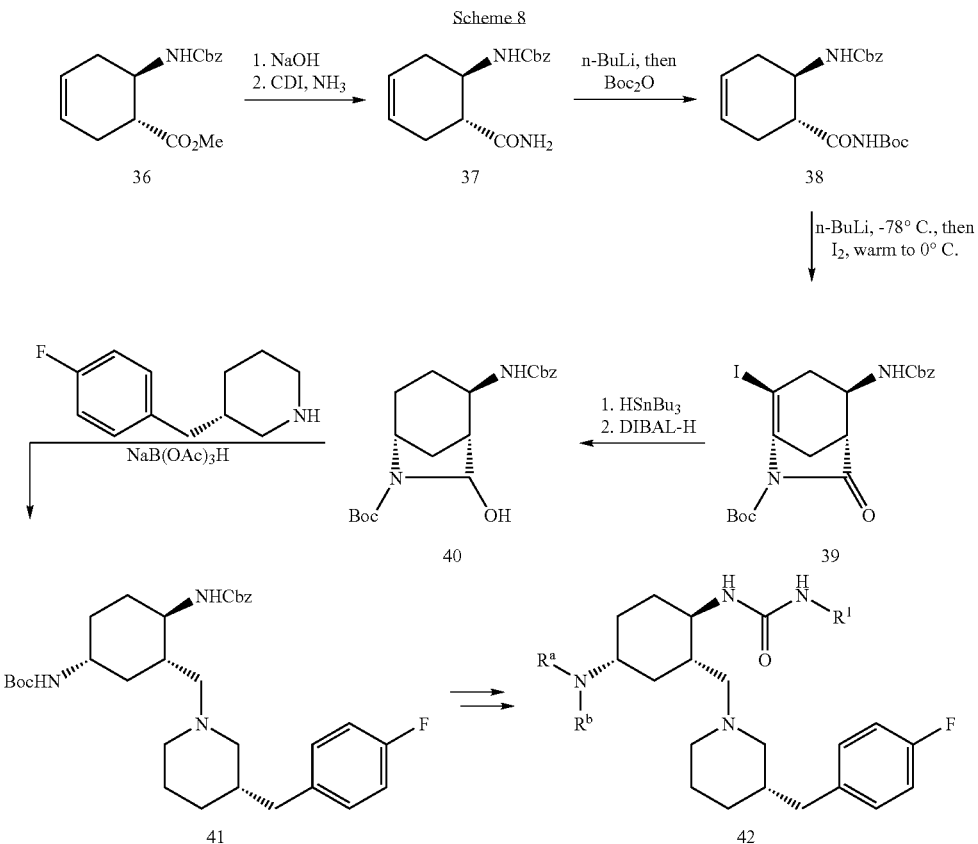

The process for forming the diastereomer of compound 39 is described in copending patent application Ser. No. 10/776,828, filed Feb. 11, 2004, the description of the process is hereby incorporated by reference. The compound 39 can be deiodinated as described in that patent application. The lactam carbonyl can be reduced using a variety of reducing agents known to one skilled in the art. Examples of reducing agents are DIBAL-H, LiEt$_3$BH (Superhydride) and LAH. Other reducing agents may also be used in this reactions The reactions are typically run in ether solvents such as diethyl ether or THF or methylene chloride or other non-reactive solvents. The reactions are typically run at temperatures of about −78° C. to about 0° C.

The reductive amination of compound 40 to 41 may occur by a variety of methods known to one skilled in the art. The reductive amination is typically run using Na(OAc)$_3$BH, NaCNBH$_3$, or Ti(iPrO)$_3$ with NaBH$_4$. Depending on the specific reagent, the reaction may be run in halogenated solvents such as methylene chloride or dichloroethane, or alcoholic solvents such as methanol or ethanol.

More generally, the compounds may be prepared using the procedure shown in Scheme 9.

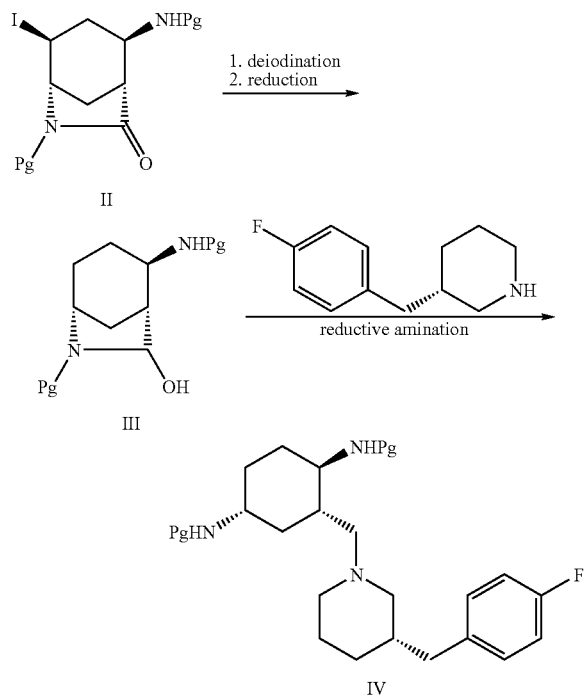

SCHEME 9 wherein Pg are amine protecting groups which may be selectively removed from the compound of formula (IV) so that the amine may be further selectively reacted to form the compounds of formula (I).

Utility

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compound of the present invention have activity in inhibition of the migration of eosinophils in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at 1×10$^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 μl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30-45 seconds. The filter is rinsed with distilled water for 7 minutes, rinsed once with water briefly, and allowed to dry. Migrated cells are enumerated by microscopy.

The utility of the compounds in accordance with the present invention as modulators of chemokine receptor activity may be demonstrated by methodology known in the art, such as the assays for CCR-1 ligand binding. In particular, the compound of the present invention have activity in binding to the CCR-1 receptor in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A general binding protocol is described below.

A, Cells

CCR1 Expressing Cells a. THP-1 Cells

THP-1 cells are obtained from ATCC (Manassas, Va.) and cultured as a suspension in RPMI-1640 medium supplemented with 2 mM L-glutamine, penicillin/streptomycin, and 10% FBS. Cells are grown under 5% $CO_2$/95% air, 100% humidity at 37° C. and subcultured twice weekly at 1:5 and harvested at $1\times10^6$ cells/ml. THP-1 cells express CCR1 and can be used in CCR1 binding and functional assays.

b. CCR1-Transfected CHO Cells

Human CCR1 cDNA is purchased from ATCC and cloned into the pcDNA3 expression vector (Introgen, San Diego, Calif.). CCR1-pcDNA3 is introduced into CHO cells (ATCC) by electroporation and stable integrants are selected by growth in G418-containing media. High-expressing cell lines are identified by radioligand binding assays and then subsequently maintained in DMEM with 10% FBS and 200 μg/ml G418.

c. Isolated Human Monocytes

Monocytes are isolated from the peripheral blood of human healthy donors using magnetic bead separation. Briefly, following Ficoll gradient separation to isolate a mononuclear fraction, cells are washed with PBS and the red blood cells lysed using standard procedures. Remaining cells are labeled with anti-CD14 antibodies coupled to magnetic beads (Miltenyi Biotech, Auburn, Calif.). Labeled cells are passed through an AutoMACS (Miltenyi, Aubum, Calif.) and the positive fraction collected. Monocytes express CCR1 and can be used in CCR1 binding and functional assays.

B. Assays

Inhibition of CCR1 Ligand Binding a. Whole Cell Binding

CCR1-expressing cells are centrifuged and resuspended in assay buffer (RPMI 1640, 20 mM HEPES pH 7.4, with 0.1% bovine serum albumin) to a concentration of $1.7\times10^6$ cells/mL. Compound is diluted in assay buffer and 0.05 mL are added to the assay plate. An equivalent volume of cell suspension is then added to give a final density of $2.5\times10^5$ THP-1 cells/well. 0.05 mL of $^{125}$I labeled human MIP-1α (NEN/Perkin Elmer; Boston, Mass.) diluted in assay buffer to a final concentration of 40 pM, yielding 30,000 cpm per well, is added and the plates incubated for approximately 60 minutes at room temperature. Reactions are aspirated onto GF/B glass filters pre-soaked in 0.3% polyethyleneimine (PEI) solution, on a vacuum cell harvester (Packard Instruments; Meriden, Conn.). Scintillation fluid (50 μl; Microscint 20, Packard Instruments) is added to each well, the plates sealed and radioactivity measured in a Top Count scintillation counter (Packard Instruments). Control wells contain either diluent only (for total binding) or excess MIP-1α (for non-specific binding). The percent inhibition of specific binding is calculated from duplicate wells. If a graded series of compound concentrations has been used, the percent inhibition is plotted against compound concentration using computer software (GraphPad Prism, San Diego, Calif.) and the $IC_{50}$ obtained.

b. Membrane Binding

The procedure is similar to that for whole cells, but utilizes membranes from CHO cells stably transfected with human CCR1 (Amersham, Piscataway, N.J.). To wells containing diluted compound, 0.05 mL of membrane are added to a final concentration of 950 μg/mL. $^{125}$I labeled MIP-1α is added at the same concentration as for whole cells and the plates incubated for approximately 60 minutes at room temperature. After incubation, the plates are washed with buffer (RPMI 1640, 20 mM HEPES with 0.1% bovine serum albumin and 0.4 M NaCl), aspirated and air-dried. The plates are counted in gamma counter (Packard Instruments).

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compound of the present invention have activity in inhibition of the migration of eosinophils in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A human eosinophil chemotaxis assay protocol is described below.

Chemotaxis Assay

THP-1 cells ($3\times10^7$) are loaded with Calcein-AM fluorescent dye (Molecular Probes; Eugene, Oreg.) in cell medium for 30 minutes at 37° C. and washed with pre-warmed chemotaxis buffer (RPMI 1640 phenol red-free, with 0.1% bovine serum albumin). The assay is performed in a 96-well chemotaxis plate (BD Falcon Fluoroblok, Bedford, Mass.) in which each well contains upper and lower chambers separated by a polycarbonate, polyvinylpyrrolidone-coated filter containing pores of 8 micron diameter. Lower chambers are each loaded with 225 μL of buffer containing MIP-1α (i.e., 1-100 ng/mL) and compound. Top chambers are each loaded with 50 μL of buffer containing $5\times10^4$ cells. The plates are incubated for 30-60 minutes at 37° C. The chemotactic migration of cells through the filter is quantified either by determining the levels of fluorescence in the lower chamber, using a Cytofluor at an excitation wavelength of 485 nm and emission wavelength of 530 nm (PE Biosystems, Stafford, Tex.), or by directly counting the cells on the undersurface of the filter using a microscope.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 μM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Additional diseases or conditions of human or other species which can be treated with inhibitors of chemokine receptor function, include, but are not limited to: Alzheimer's disease, Rheumatoid arthritis, Psoriatic arthritis, Juvenile arthritis, Sjogren's syndrome, Ankylosing spondylitis, Gout, Allograft rejection, Xenograft rejection, Lupus, including systemic lupus erythematosus, Atherosclerosis, Restenosis, Ischemia reperfusion injury, Thrombosis, Wegener's syndrome, Goodpasture's syndrome, Giant cell arteritis, Polyarteritis nodosa, Inflammatory bowel disease, Crohn's disease, Ulcerative colitis, Psoriasis, Multiple sclerosis, Systemic sclerosis, Hepatic sclerosis, Pulmonary fibrosis, Cystic fibrosis, Fibrosis caused by radiation or bleomycin, Idiopathic pulmonary fibrosis, Chronic bronchitis, Chronic obstructive pulmonary disease, Adult respiratory distress syndrome, Respiratory distress syndrome of infant, Immune complex alveolitis, Asthma, Anaphylaxis, Pemphigus, Contact dermatitis, Atopic dermatitis, Pancreatitis-associated injury, Congestive heart failure, Pulmonary emphysema, Viral induced encephalomyelitis or demylination, Neurodegenerative diseases including prion disease, HIV-associated dementia, Sandhoff disease, Viral inflammation of the lung or liver, Influenza virus pneumonia, Severe acute respiratory syndrome, Hepatitis C, Schistosomiasis, Cytomegalovirus, Adenoviruses, Herps viruses, Fungal meningitis, Lyme disease, and Malaria.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis, Hookworm, Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a nonsteroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflunic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

It is desirable to find new compounds with improved pharmacological characteristics compared with known CCR-3 inhibitors. For example, it is desirable to find new compounds with improved CCR-3 inhibitory activity and selectivity for CCR-3 versus other G protein-coupled receptors (i.e. 5HT2A receptor). It is also desirable to find compounds with advantageous and improved characteristics in one or more of the following categories:

(a) pharmaceutical properties (i.e. solubility, permeability, amenability to sustained release formulations); (b) dosage requirements (e.g., lower dosages and/or once-daily dosing); (c) factors which decrease blood concentration peak-to-trough characteristics (i.e. clearance and/or volume of distribution); (d) factors that increase the concentration of active drug at the receptor (i.e. protein binding, volume of distribution); (e) factors that decrease the liability for clinical drug-drug interactions (cytochrome P450 enzyme inhibition or induction, such as CYP 2D6 inhibition, see G K Dresser, J D Spence, D G Bailey Clin. Pharmacokinet. 2000, 38, 41-57, which is hereby incorporated by reference); (f) factors that decrease the potential for adverse side-effects (i.e. pharmacological selectivity beyond G protein-coupled receptors, potential chemical or metabolic reactivity, limited CNS penetration) (g) factors that improve manufacturing costs or feasibility (i.e. difficulty of synthesis, number of chiral centers, chemical stability, ease of handling).

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the inflammatory disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I)

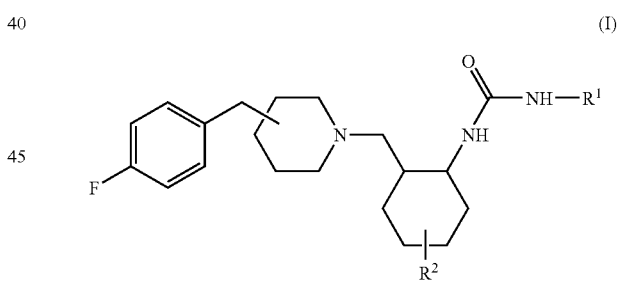

or stereoisomers or pharmaceutically acceptable salts thereof, wherein:

$R^1$ is selected from $C_{1-6}$ alkyl, a $(CH_2)_r$—$C_{3-10}$ carbocyclic residue substituted with 0-5 $R^5$ and a $(CH_2)_r$-5-10 membered heterocyclic system containing 1-4 heteroatoms selected from N, O, and S, substituted with 0-3 $R^5$;

$R^2$, at each occurrence, is $NR^{4a}R^{4a}$;

$R^{4a}$, at each occurrence, are selected from H, $C_{1-6}$ alkyl, $C_{2-8}$ alkenyl, $C_{2-8}$ alkynyl, a $(CH_2)_rC_{3-10}$ carbocyclic residue substituted with 0-5 $R^{4e}$, and a $(CH_2)_r$-5-10 membered heterocyclic system containing 1-4 heteroatoms selected from N, O, and S, substituted with 0-2 $R^{4e}$;

alternatively, two $R^{4a}$ join to form a 5, 6, or 7-membered ring containing from 0-1 additional heteroatoms selected from N and O, the ring containing 0-1 C=O and being substituted with 0-1 $R^f$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, ON, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, and $(CH_2)_r$phenyl;

$R^{4f}$, at each occurrence, is selected from H, $C_{1-6}$ alkyl, $C_{3-6}$ cycloalkyl, and phenyl;

$R^f$, at each occurrence, is selected from H, $C_{1-6}$ alkyl, $C_{3-6}$ cycloalkyl, and phenyl;

$R^5$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, ON, $(CHR')_rNR^{5a}R^{5a}$, $(CHR')_rOH$, $(CHR')_rO(CHR')_rR^{5d}$, $(CHR')_rSH$, $(CHR')_rC(O)H$, $(CHR')_rS(CHR')_rR^{5d}$, $(CHR')_rC(O)OH$, $(CHR')_rC(O)(CHR')_rR^{5b}$, $(CHR')_rC(O)NR_{5a}R^{5a}$, $(CHR')_rNR^{5f}C(O)(CHR')_rR^{5b}$, $(CHR')_rC(O)O(CHR')_rR^{5d}$, $(CHR')_rOC(O)(CHR')_r R_{5b}$, $(CHR')_rC(=NR^{5f})NR^{5a}R^{5a}$, $(CHR')_r NHC(=NR^{5f})NR^{5f}R^{5f}$, $(CHR')_rS(O)_p(CHR')_rR^{5b}$, $(CHR')_rS(O)_2NR^{5a}R^{5a}$, $(CHR')_rNR^{5f}S(O)_2(CHR')_rR^{5b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{5e}$, and a $(CH_2)_r$-5-10 membered heterocyclic system containing 1-4 heteroatoms selected from N, O, and S, substituted with 0-2 $R^{5e}$;

$R^{5a}$, at each occurrence, are selected from H, $C_{1-6}$ alkyl, $C_{2-8}$ alkenyl, $C_{2-8}$ alkynyl, a $(CH_2)_rC_{3-10}$ carbocyclic residue substituted with 0-5 $R^{5e}$, and a $(CH_2)_r$-5-10 membered heterocyclic system containing 1-4 heteroatoms selected from N, O, and 3, substituted with 0-2 $R^{5e}$;

$R^{5b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0-3 $R^{5e}$, and $(CH_2)_r$-5-6 membered heterocyclic system containing 1-4 heteroatoms selected from N, O, and S, substituted with 0-2 $R^{5e}$;

$R^{5d}$, at each occurrence, is selected from $C_{2-8}$ alkenyl, $C_{2-8}$ alkynyl, $C_{1-6}$ alkyl substituted with 0-3 $R^{5e}$, a $(CH_2)_r$—$C_{3-10}$ carbocyclic residue substituted with 0-3 $R^{5e}$, and a $(CH_2)_r$5-6 membered heterocyclic system containing 1-4 heteroatoms selected from N, O, and S, substituted with 0-3 $R^{5e}$;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, ON, $NO_2$, $(CF_2)_rCF_3$, $(CH_2)_rOC_{1-5}$ alkyl, ON, SN, $(CH_2)_rSC_{1-5}$ alkyl, $(CH_2)_rNR^{5f}R^{5f}$, and $(CH_2)_r$phenyl;

$R^{5f}$, at each occurrence, is selected from N, $C_{1-6}$ alkyl, $C_{3-6}$ cycloalkyl, and phenyl;

R', at each occurrence, is selected from H and $C_{1-6}$ alkyl;

r is selected from 0, 1, 2, 3, 4, and 5; and p is selected from 0, 1, and 2.

2. The compound of claim 1, wherein:

$R^1$ is selected from $C_{1-6}$ alkyl, a $(CH_2)_r$-carbocyclic residue substituted with 0-5 $R^5$, wherein the carbocyclic residue is selected from phenyl, $C_{3-6}$ cycloalkyl, naphthyl, and adamantyl; and a $(CH_2)_r$-heterocyclic system substituted with 0-3 $R^5$, wherein the heterocyclic system is selected from pyridinyl, thiophenyl, furanyl, indazolyl, benzo[1,3]dioxolyl benzothiazolyl, benzimidazolyl, benzothiophenyl, benzofuranyl, benzoxazolyl, benzisoxazolyl, quinolinyl, isoquinolinyl, imidazolyl, indazolyl, indolyl, indolinyl, isoindolyl, isothiadiazolyl, isoxazolyl, 4-oxo-4,5-dihydro-thiazol-2-yl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

3. The compound of claim 2, wherein:

$R^2$, at each occurrence, is $NR^{4a}R^{4a}$;

$R^{4a}$, at each occurrence, are selected from H, $C_{1-6}$ alkyl, $C_{3-6}$ cycloalkyl, and $(CH_2)_r$phenyl substituted with 0-3 $R^{4e}$, and a $(CH_2)_r$-5-6 membered heterocyclic system containing 1-4 heteroatoms selected from N, O, and S, substituted with 0-2 $R^{4e}$;

alternatively, two $R^{4a}$ join to form a 5, 6, or 7-membered ring containing from 0-1 additional heteroatoms selected from N and O, wherein the ring is selected from pyrrolidinyl, piperidinyl, morpholinyl and piperazinyl, the ring containing 0-1 C=O and being substituted with 0-1 $R^f$;

$R^{4e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^f$, at each occurrence, is selected from H, methyl, ethyl, propyl, i-propyl, butyl, pentyl, hexyl, cyclopropyl, cyclopentyl, cyclohexyl, and phenyl; and r is selected from 0, 1, and 2.

4. The compound of claim 3, wherein:

$R^1$ is selected from $C_{1-6}$ alkyl selected from methyl, ethyl, propyl, i-propyl, and butyl, a $C_{3-10}$ carbocyclic residue substituted with 0-3 $R^5$, wherein the carbocyclic residue is selected from cyclopropyl, cyclopentyl, cyclohexyl, phenyl, naphthyl and adamantyl, and a $(CH_2)_r$-heterocyclic system substituted with 0-3 $R^5$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzoisoxazolyl, quinolinyl, isoquinolinyl, imidazolyl, indazolyl, indolyl, indolinyl, isoindolyl, isothiadiazolyl, isoxazolyl, 4-oxo-4,5-dihydro-thiazol-2-yl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$, at each occurrence, is selected from $C_{1-8}$ alkyl, $(CH_2)_rC_{3-6}$ cycloalkyl, $CF_3$, Cl, Br, I, F, $(CH_2)_rNR^{5a}R^{5a}$, $NO_2$, CN, OH, $(CHR')_rOR^{5d}$, $(CH_2)_rC(O)R^{5b}$, $(CH_2)_rC(O)OR^{5d}$, $(CH_2)_rC(O)NR^{5a}R^{5a}$, $(CH_2)_rNR^{5f}C(O)R^{5b}$, $(CH_2)_rS(O)_pR^{5b}$, $(CH_2)_rS(O)_2NR^{5a}R^{5a}$, $(CH_2)_rNR^{5f}S(O)_2R^{5b}$, $(CH_2)_r$phenyl substituted with 0-3 $R^{5e}$, and a $(CH_2)_r$-5-6 membered heterocyclic system containing 1-4 heteroatoms selected from N, O, and S, substituted with 0-2 $R^{5e}$;

$R^{5a}$, at each occurrence, are selected from H, $C_{1-6}$ alkyl, $C_{3-6}$ cycloalkyl, and $(CH_2)_r$phenyl substituted with 0-3 $R^{5e}$;

$R^{5b}$, at each occurrence, is selected from H, $C_{1-6}$ alkyl, $C_{3-6}$ cycloalkyl, and $(CH_2)_r$phenyl substituted with 0-3 $R^{5e}$;

$R^{5d}$, at each occurrence, is selected from $C_{1-6}$ alkyl and phenyl;

$R^{5e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{5f}$, at each occurrence, is selected from H, and $C_{1-5}$ alkyl.

5. The compound of claim 4, wherein:

$R^1$ is selected from $C_{1-5}$ alkyl selected from methyl, ethyl, propyl, i-propyl, and butyl, a $C_{3-10}$ carbocyclic residue substituted with 0-2 $R^5$, wherein the carbocyclic residue is selected from cyclopropyl, cyclopentyl, cyclohexyl, phenyl and adamantyl, and a heterocyclic system substituted with 0-3 $R^5$, wherein the heterocyclic system is selected from pyridinyl, indazolyl, benzo[1,3]dioxolyl, benzothiazolyl, benzoxazolyl, benzisoxazolyl, 2,3-dihydroindolyl, indolyl, indazolyl, indolinyl, isoxazolyl, 4-oxo-4,5-dihydro-thiazol-2-yl, pyrrazolyl, pyrimidinyl, 1,2,4-triazolyl, 1,2,3-triazolyl, tetrazolyl, thiadiazolyl, thiazolyl, and oxazolyl; and $R^5$, at each occurrence, is selected from methyl, ethyl, propyl, i-propyl, butyl, s-butyl, i-butyl, t-butyl, pentyl, hexyl, cyclopropyl, $CF_3$, Cl, Br, I, F, CN, OH, $(CHR')_r$ $OR^{5d}$, $C(O)R^{5b}$, $C(O)OR^{5d}$, $C(O)NR^{5a}R^{5a}$, $(CH_2)_rS(O)_pR^{5b}$, $(CH_2)NR^{5f}S(O)_2R^{5b}$, $(CH_2)_r$phenyl substituted with 0-3 $R^{5e}$, and a $(CH_2)_r$-5-6 membered heterocyclic system containing 1-4 heteroatoms selected from N, O, and S, substituted with 0-2 $R^{5e}$, wherein the heterocyclic system is selected from tetrazolyl, imidazolyl, pyrimidinyl, pyrrolidinyl, and isoxazolyl;

$R^{5a}$, at each occurrence, are selected from H, methyl, ethyl, propyl, i propyl, butyl, s-butyl, i-butyl, t-butyl, pentyl, and hexyl;

$R^{5b}$, at each occurrence, is selected from H, methyl, ethyl, propyl, i-propyl, butyl, s-butyl, i-butyl, t-butyl, pentyl, and hexyl;

$R^{5d}$, at each occurrence, is selected from methyl, ethyl, propyl, i propyl, butyl, s-butyl, i-butyl, t-butyl, pentyl, and hexyl; and $R^{5e}$, at each occurrence, is selected from methyl, ethyl, propyl, i propyl, butyl, s-butyl, i-butyl, t-butyl, pentyl, and hexyl.

6. The compound of claim 5, wherein:

$R^2$, at each occurrence, is $NR^{4a}R^{4a}$;

$R^{4a}$, at each occurrence, are selected from H, methyl, ethyl, propyl, j propyl, butyl, s-butyl, i-butyl, t-butyl, pentyl, hexyl, cyclopropyl, cyclobutyl, cyclopentyl, and cyclohexyl;

alternatively, two $R^{4a}$ join to form a 5, 6, or 7-membered ring containing from 0-4 additional heteroatoms selected from N and O, wherein the ring is selected from pyrrolidinyl, piperidinyl, morpholinyl and piperazinyl, the ring being substituted with 0-1 $R^f$;

$R^f$, at each occurrence, is selected from H, methyl, ethyl, propyl, and i-propyl.

7. A pharmaceutical composition comprising a pharmaceutically acceptable carrier and a therapeutically effective amount of a compound according to claim 1, or a pharmaceutically acceptable salt thereof.

\* \* \* \* \*

UNITED STATES PATENT AND TRADEMARK OFFICE
CERTIFICATE OF CORRECTION

PATENT NO. : 7,550,486 B2
APPLICATION NO. : 11/972649
DATED : June 23, 2009
INVENTOR(S) : Soo Ko et al.

It is certified that error appears in the above-identified patent and that said Letters Patent is hereby corrected as shown below:

Column 76, Line 37, Claim 1, after "formula (I)" insert -- : --.

Column 77,

Line 3, Claim 1, delete "ON," and insert -- CN, --.

Line 11, Claim 1, delete "ON," and insert -- CN, --.

Line 14, Claim 1, delete "$(CHR')_rC(O)NR_{5a}R^{5a}$," and insert

-- $(CHR')_rC(O)NR^{5a}R^{5a}$, --.

Line 16, Claim 1, delete "$(CHR')_rR_{5b}$," and insert -- $(CHR')_rR^{5b}$, --.

Line 28, Claim 1, delete "3," and insert -- S, --.

Line 42, Claim 1, delete "ON," and insert -- CN, --.

Line 42, Claim 1, delete "ON, SN," and insert -- OH, SH, --.

Line 44, Claim 1, delete "N," and insert -- H, --.

Line 46, Claim 1, delete "alkyl,;" aind insert -- alkyl; --.

Line 61, Claim 2, delete "pyrrazolyl", and insert -- pyrazolyl, --.

Signed and Sealed this

Eighth Day of June, 2010

David J. Kappos
*Director of the United States Patent and Trademark Office*

Column 78,

Line 26, Claim 4, delete "benzoisoxazolyl," and insert -- benzisoxazolyl, --.

Line 29, Claim 4, delete "pyrrazolyl," and insert -- pyrazolyl, --.

Line 53, Claim 5, delete "$C_{1-5}$ alkyl" and insert -- $C_{1-6}$ alkyl --.

Line 62, Claim 5, delete "pyrrazolyl," and insert -- pyrazolyl, --.

Column 79,

Line 2, Claim 5, delete "$(CH_2)NR^{5f}S(O)_2R^{5b}$," and insert -- $(CH_2)_rNR^{5f}S(O)_2R^{5b}$, --.

Line 9, Claim 5, delete "i propyl," and insert -- i-propyl, --.

Line 15, Claim 5, delete "i propyl," and insert -- i-propyl, --.

Line 18, Claim 5, delete "i propyl," and insert -- i-propyl, --.

Column 80,

Line 4, Claim 6, delete "j propyl," and insert -- i-propyl, --.

Line 8, Claim 6, delete "0-4" and insert -- 0-1 --.